United States Patent [19]

Floyd, Jr.

[11] 4,233,453
[45] Nov. 11, 1980

[54] 15-DEOXY-16-HYDROXY-16-ALLENYL PROSTANE DERIVATIVES OF THE E AND F SERIES

[75] Inventor: Middleton B. Floyd, Jr., Suffern, N.Y.

[73] Assignee: American Cyanamid Company, Stamford, Conn.

[21] Appl. No.: 46,512

[22] Filed: Jun. 7, 1979

[51] Int. Cl.³ .................................... C07L 177/00
[52] U.S. Cl. ......................... 560/121; 260/410.9 R; 260/413; 260/438.1; 562/503; 568/873; 424/305; 424/317; 568/397; 568/417; 556/482

[58] Field of Search .................. 560/121; 562/503; 260/410.9 R, 413

Primary Examiner—Robert Gerstl
Attorney, Agent, or Firm—Richard J. Hammond

[57] ABSTRACT

This invention disclosed herein relates to pharmacologically active 15-deoxy-16-hydroxy prostaglandin derivatives of the E and F series wherein $C_{16}$ is substituted with allenyl.

These compounds are active as hypotensives, antisecretory, bronchodilating and fertility control agents.

4 Claims, No Drawings

15-DEOXY-16-HYDROXY-16-ALLENYL PROSTANE DERIVATIVES OF THE E AND F SERIES

BACKGROUND OF THE INVENTION

(1) Field of the Invention

The present invention relates to 15-deoxy-16-hydroxy-16-allenyl prostaglandins, as well as the pharmaceutically acceptable, non-toxic lower alkyl esters and salts thereof, and to the intermediates and processes for producing such compounds.

(2) Description of the Prior Art

Prostaglandins have classically been described as chemically related 20 carbon chain hydroxy fatty acids having the basic skeleton of prostanoic acid:

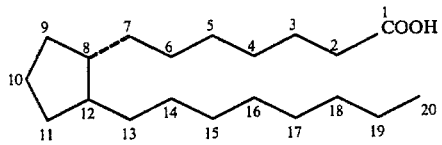

The prostaglandins having a hydroxyl group at the C-11 position and a keto group at the C-9 position are known as the PGE series, and those having a hydroxyl group in place of the keto group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the $PGF_1$ and $PGE_1$ series refer to prostanoic acids having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see, for example, P. Ramwell, The Prostaglandins, 1, pp. 5–22 (1973).

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axen et al, Synthesis Vol. 1, John Wiley and Sons Inc., New York, New York. 1973 and P. H. Bently, Chem. Soc. Reviews, 2, 29 (1973)].

The synthesis of prostaglandin analogs possessing a 3-oxa- or 11-deoxy-3-thia moiety have been described, among others in U.S. Pat. No. 3,873,607; U.S. Pat. No. 3,950,406; Netherlands Pat. No. 7305222-Q; U.S. Pat. No. 3,944,593; U.S. Pat. No. 3,931,289; and U.S. Pat. No. 3,936,487.

The synthesis of several prostaglandin analogs wherein the hydroxyl group at C-15 has been removed and a hydroxyl group has been introduced at C-16 has appeard [see for example, U.S. Pat. No. 3,950,406; Prostaglandins, Vol. 10, 733 (1975); Tetrahedron Letters, No. 48, 4217 (1975)].

Recently, reports have also appeared wherein the C-16 carbon bearing a hydroxyl group is substituted with a methyl group [see Pappo et al., Tetrahedron Letters, No. 4, 235 (1975); Collin et al., U.S. Pat. No. 3,965,143; and Belgium Pat. No. 827,127].

Also, a patent has recently appeared wherein the C-16 carbon bearing the hydroxyl group is substituted with vinyl, methylvinyl, and cyclopropyl (U.S. Pat. No. 4,061,670).

15-Hydroxy prostaglandins substituted with allenyl at C-4, C-5 and C-6 have been described in U.S. Pat. Nos. 3,873,598, 3,879,438, 3,970,684 and 3,985,971. 16-Hydroxy prostaglandins substituted with allenyl at C-13, C-14 and C-15 have been reported in Prostaglandins, 14, No. 5, 807 (1977).

SUMMARY OF THE PRESENT INVENTION

In accordance with the present invention, we have prepared certain novel 15-deoxy-16-hydroxy-16-allenyl prostaglandin analogs represented by the following formula:

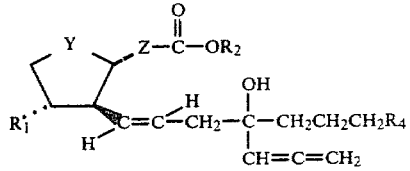

wherein Y is

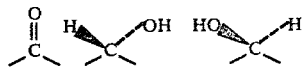

$R_1$ is selected from the group consisting of hydrogen and hydroxyl;

$R_2$ is selected from the group consisting of hydrogen and $C_1$–$C_6$ alkyl;

$R_4$ is selected from the group consisting of hydrogen and $C_1$–$C_3$ alkyl and chlorine, a preferred embodiment is when $R_4$ is hydrogen and $C_1$–$C_3$ alkyl;

Z is selected from the group consisting of a divalent moiety of the formulae: $-(CH_2)_n-$, $-(CH_2)_mSCH_2-$, $-(CH_2)_mOCH_2-$, and $-CH_2CH=CH(-CH_2)_p-$, wherein m is 3 to 5, preferably 4, n is 5 to 7, preferably 6, and p is 2 to 4, preferably 3; the racemic mixture thereof; and when $R_1$ is hydrogen; the pharmacologically acceptable salts thereof.

The dotted lines shown in the above formula and in the formulas below indicate that the substituents are in the α configuration, i.e., below the plane of the cyclopentane ring.

The double bond at C-13 in the compounds of the present invention has the same configuration as in natural prostaglandins of the PGE and PGF series, that is the trans configuration.

These novel compounds possess asymmetric centers and thus can be produced as racemic mixtures or as individual enantiomers. The racemic mixtures can be resolved if desired at appropriate stages by methods known to those skilled in the art, to obtain the respective individual enantiomers. It is to be understood that the racemic mixtures and the individual 8R-enantiomers are encompassed within the scope of the present invention.

When the compounds of the present invention are racemic mixtures, they are produced starting from racemates, while when the compounds of the invention are individual enantiomers the compounds are preferably obtained starting from the appropriate individual enantiomer.

Useful pharmacologically acceptable salts of the above formula, where $R_1$ is hydrogen, are those with pharmacologically acceptable metal cations, ammonium, amine cations or quaternary ammonium cations.

Preferred metal cations are those derived from the alkali metals, e.g., lithium, sodium and potassium, and from the alkaline earth metals, e.g., magnesium and calcium, although cationic forms of other metals, e.g. aluminum, zinc and iron, are within the scope of this invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenyethylamine, ethylenediamine, and arylipatic amines containing up to and including 18 carbon atoms, as well as heterocyclic amines, e.g., piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris-(hydroxymethyl)-aminomethane, N-phenylethanolamine, N-(p-tertamylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The novel compounds of this invention can be prepared by a 1,4-conjugate-addition procedure involving treatment of the ether blocked cyclopentenone (11) with a lithio-cuprate reagent such as (8), (9) or (10) prepared as illustrated in Flowsheets A, B, C and D.

Although Flowsheets A and B exemplify the use of a trimethylsilyloxy protecting group, any protecting group which survives the conjugate addition reaction described by these tables and the examples of this application may be employed. Suitable protecting groups therefore include tri($C_1$-$C_4$)alkylsilyl, or other acid labile protecting groups such as tetrahydropyranyl, tetrahydrofuranyl, or other acetals. Moreover, with reference to the lithiocuprates of Flowsheet B (structures 8, 9 or 10) in addition to the lithiocuprates described, the intermediates of structures (14) and (15) may also be employed.

In this specification the terms 16-propadienyl and 16-allenyl are used interchangeably and both refer to the group $-CH=C=CH_2$.

Flowsheet A

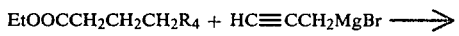

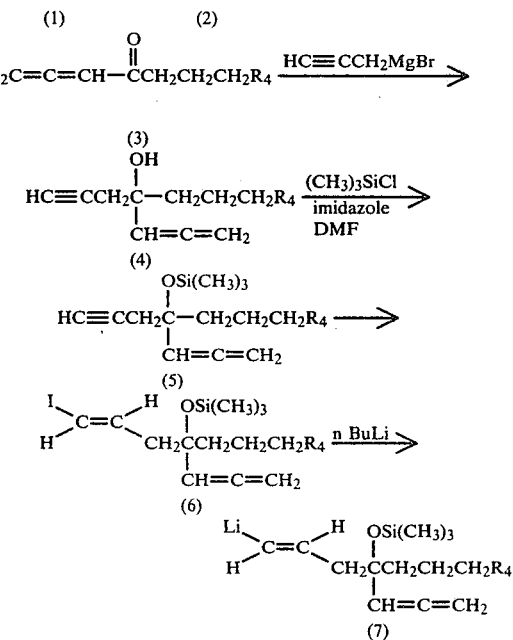

In accordance with the procedure outlined in Flowsheet A, treatment of esters such as (1) with propargyl grignard reagent (2) wherein $R_4$ is hydrogen, methyl, ethyl, propyl or chloro provides the allenylketone (3). Treatment of the ketone (3) with propargylmagnesium bromide provides the hydroxyalkyne (4) which is silylated to give the ether (5). The alkyne (5) is converted to the trans vinyliodide (6) by successive treatment with disiamylborane, triethylamine oxide and $I_2$/NaOH as described by Kluge, et al, J. Amer. Chem. Soc., 94, 7827 (1972). Treatment of the vinyliodide (6) with one equivalent of n-butyl lithium at $-70°$ C. to $-50°$ C. affords the vinyl lithium reagents (7).

Flowsheet B

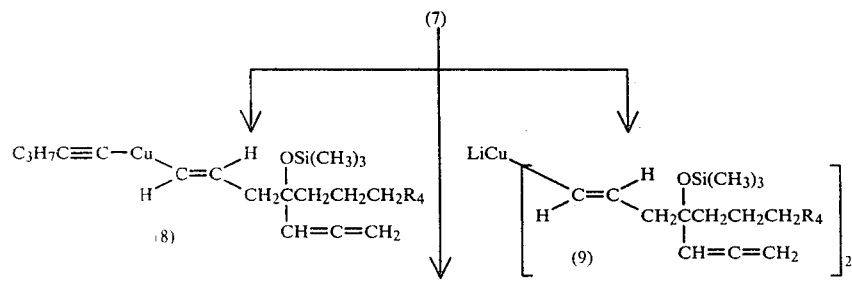

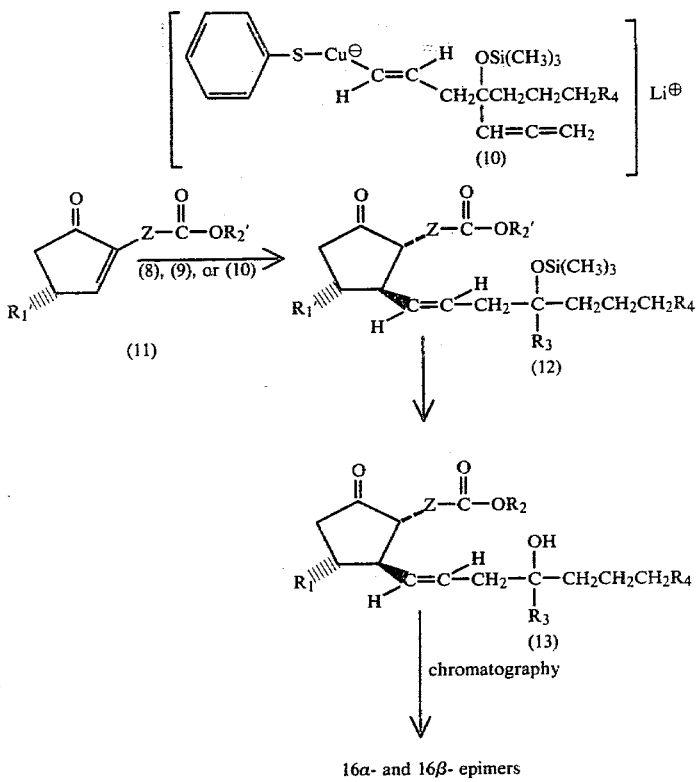

wherein $R_2'$ is lower alkyl $C_1$-$C_6$, tetrahydropyranyl, or trilower($C_1$-$C_3$) alkylsilyl;

$R_1'$ is hydrogen, tetrahydropyranyloxy, or trilower ($C_1$-$C_3$) alkylsilyloxy;

$R_1$, $R_2$ are as hereinabove defined; Z is $(CH_2)_n$, $(CH_2)_m OCH_2$, $(CH_2)_m SCH_2$ or

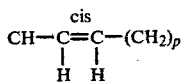

wherein m,n and p are as previously defined.

In accordance with Flowsheet B for the preparation of the asymmetrical lithio-cuprate (8) wherein $R_3$ is —CH=C=CH$_2$, a solution of one molar equivalent of copper (I)-1-alkyne, preferably copper (I)-1-pentyne in anhydrous tributylphosphine or HMPTA, preferably one to five molar equivalents, in ether is added to one molar equivalent of the aforementioned vinyl lithium solution cooled to about −78° C. After about one hour at this temperature, a molar equivalent of the requisite cyclopentenone (11) is added. After several hours at −30° C. to −70° C. the reaction mixture is quenched with aqueous ammonium chloride solution and the blocked product (12) is isolated in the usual manner.

It is also possible to effect conjugate 1,4-addition with the asymmetrical lithio-cuprate (10) wherein $R_4$ is as previously defined derived from vinyl lithium and cuprous thiophenoxide. A solution of vinyl lithium (7) in ether at −78° C. is reacted with an equimolar amount of a reagent prepared by admixture, in ether at a temperature of 0° C. to −78° C., of equimolar amounts of cuprous thiophenoxide and copper (I) iodide tributlyphosphonium complex. After about 30 minutes at this temperature, the lithio-cuprate is treated with the requisite cyclopentenone (11) as described hereinabove for the conjugate addition with 1-alkynyl lithio-cuprate (8).

For the preparation of the symmetrical lithio-cuprate (9) wherein $R_4$ is as previously defined, one molar equivalent of copper (I) iodide tributylphosphine complex, dissolved in anhydrous ether, is added at about −78° C. to two molar equivalents of the aforementioned vinyl lithium (7) solution cooled to −78° C. After about one hour at this temperature, the lithio cuprate (9) is treated with the requisite cyclopentenone (11) as described hereinabove for the conjugate addition with the 1-alkynyl lithio-cuprate.

The procedures for conjugate addition involving organocopper reagents are well known in the art; see for example C. J. Sih, et al, J. Amer. Chem. Soc., 97, 865 (1975), which is incorporated by reference.

In the cases where $R'_1$=trimethylsilyloxy in cyclopentenone (11) the conjugate addition is performed at −78° C. to −40° C. The reaction is quenched by addition of an ether solution of acetic acid. Removal of blocking groups is then carried out as described in the reference above to provide the product (13) wherein $R_1$, $R_2$, and $R_4$ are as hereinabove.

The introduction of a racemic β-chain possessing the 16-hydroxy-16-allenyl moiety provides a pair of prostaglandins epimeric at C-16. These two epimers may be separated into their upper (less polar) and lower (more polar) components by high-pressure liquid chromatography (HPLC) or by dry-column or preparative thin layer silica-gel chromatography.

If an optically active protected cyclopentenone such as (11) is utilized, then HPLC separation will provide the corresponding optically active nat. 9-oxo-11α,16β- dihydroxy-16-allenyl and nat. 9-oxo-11α,16α-dihydroxy-16-allenyl-PGE enantiomers.

All available evidence leads us to believe that the

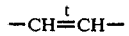

function introduced by the cuprate process occupies a position trans to the 11-oxy function. Similarly, we are led to the conclusion that in the product (12) the two side-chains attached to $C_8$ and $C_{12}$ are trans to each other. However, we are not certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8ξ. In order to ensure a trans-relationship in (13) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

The triloweralkylsilyloxy substituted lithio-cuprate reagents of type (8), (9) and (10) and the iodo precursors are novel and useful compounds which are also embraced by this invention. They may be defined by generic formulae (14) and (15)

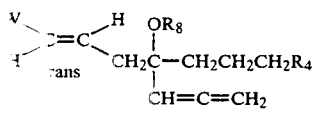

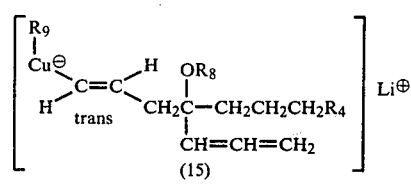

wherein W is R-Sn wherein R is tri-($C_1$–$C_6$)-alkyl and preferably a tri-n-butyl group, or W is lithium; $R_8$ is tri-$C_1$–$C_4$ alkylsilyl, preferably trimethylsilyl or other acid labile protecting groups such as tetrahydropyranyl, tetrahydrofuranyl or other acetals; $R_9$ is thiophenoxide, substituted thiophenoxide wherein the substituent may be $C_1$–$C_4$ alkyl, $C_1$–$C_4$ alkoxy, $C_1$–$C_3$ dialkylamino or phenyl, or $R_9$ may be $C_3$–$C_4$ alkyne or the identical vinyl moiety.

The cyclopentenones required for the preparation of the $E_1$, $E_2$, 3-oxa, and 11-deoxy-3-thia series have been described in the literature. The cyclopentenone for the preparation of 3-thia-11-hydroxy prostaglandins is described in Flowsheet D.

In accordance with Flowsheet D which is hereinbelow described, treatment of 2-furyl lithium (16) with a chloroaldehyde (17) provides the chloralcohol (18). Treatment of the chloroalcohol (18) with ethylmercaptoacetate furnishes the hydroxyester (19) which upon hydrolysis with sodium formate/formic acid provides the 3-hydroxy-cyclopentenone (20). Treatment of the cyclopentenone (20) with sulfuric acid provides the required 4-hydroxy-cyclopentenone (21) which after treatment with chlorotrimethylsilane provides the bis-silylated cyclopentenone (22).

Flowsheet D

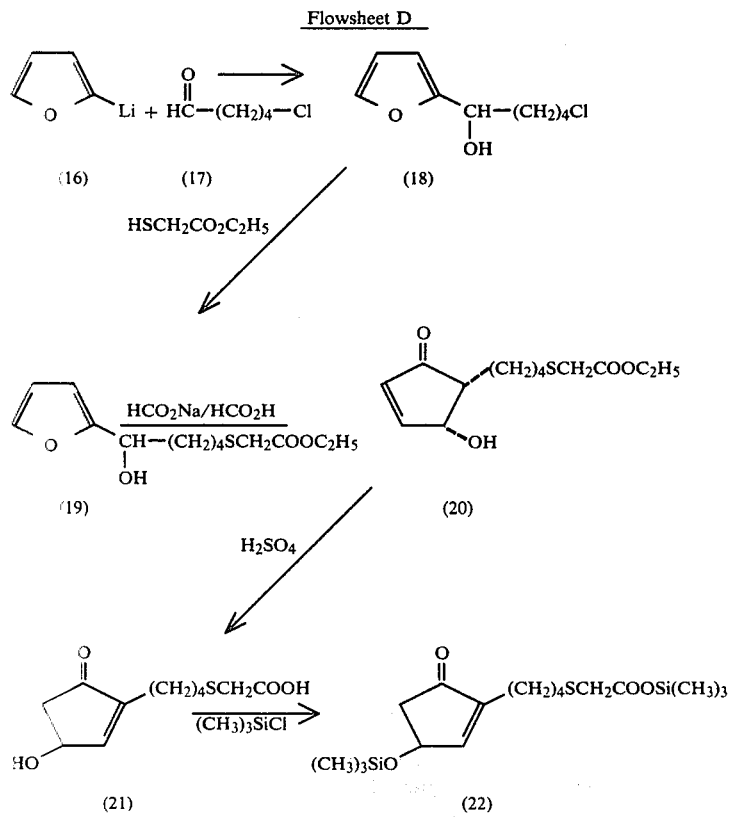

In accordance with Flowsheet D, when the 11-hydroxy or 11-oxy derivatives are treated with dilute acid, it is possible to effect elimination and the formation of the corresponding $\Delta^{10}$ derivatives (23) of the prostaglandin A-type. A preferred procedure involves treatment of tetrahydrofuran: water 2:1) solvent 0.5 N in HCl for about 30 hours at ambient temperature. Under these conditions a tetrahydropyranyl or trialkylsilyl ester or ether will undergo hydrolysis.

Flowsheet D

(12) or (13) ⟶

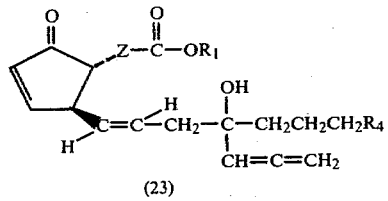

(23)

The prostaglandin carboxylic acids of this invention can be readily converted to the various alkyl esters of this invention by treatment in the usual manner with the appropriate diazoalkane. The preparation of diazoalkanes by various procedures are well described in the art. See for example, C. D. Gutsche, Organic Reactions, VIII, 389 (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydrides are then treated with the appropriate alcohol to give the derivatized product. [For a pertinent literature analogy see Prostaglandins, 4, 768 (1973).]

An alternative procedure involves treatment of the prostaglandin acid with a molar equivalent of the trialkyl amine in an excess of the appropriate alochol in an anhydrous solvent such as methylene chloride, molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279.) A third procedure involves the use of dicyclohexylcarbodiimide in the usual manner; for a pertinent literature analogy see German Offen. 2,365,205; Chem. Abst., 81, 120098 g (1974).

The esterified alcohol derivatives of this invention are also prepared in the usual manner by procedures well known in the art from the appropriate alkanoic acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19–27 (August 1973) as well as references cited therein. Additional information, concerning high speed liquid chromatography and the instruments necessary for its application, is available from Waters Associate Inc., Maple Street, Milford, Mass.].

Flowsheet E

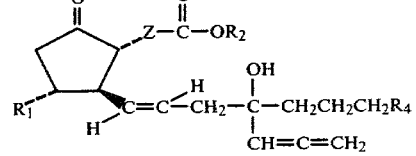

(13)

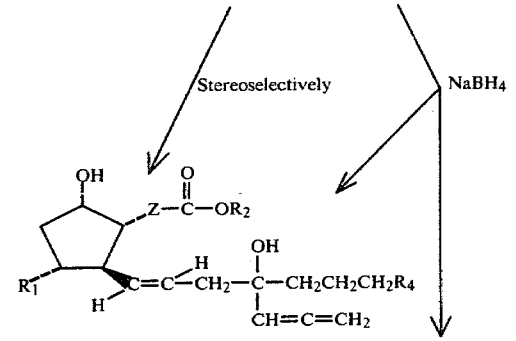

(24)

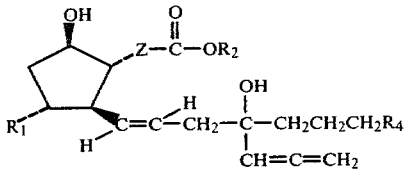

(25)

In accordance with Flowsheet E, treatment of a prostaglandin of the E series (9-oxo) (13) with a carbonyl reducing reagent such as sodium borohydride provides a mixture of the corresponding PGFα (9β-hydroxy) (24) and PGFβ (9β-hydroxy)(25) analogs. These two epimeric alcohols are readily separated by silica gel chromatography.

If one utilized the individual 16α-hydroxy or 16β-hydroxy E starting material, after separating the 9β product by silica gel chromatography, the isolated products are the 9α,16α-dihydroxy and 9α,16β-dihydroxy derivatives, respectively.

Use of a stereoselective reagent such as lithiumperhydro-9b-boraphenalylhydride [H. C. Brown and W. C. Dickason, J.A.C.S., 92, 709 (1970)] or lithium tri-sec-butylborohydride [H. C. Brown and S. Krishnamurthy, Ibid, 94, 7159 (1972)] provides the PGF product (24) as the selective species.

Likewise, utilization of either the individual 16α- or 16β-hydroxy E compounds affords the corresponding 9α,16α-dihydroxy and 9α,16β-dihydroxy prostaglandins of this invention respectively.

Flowsheet F

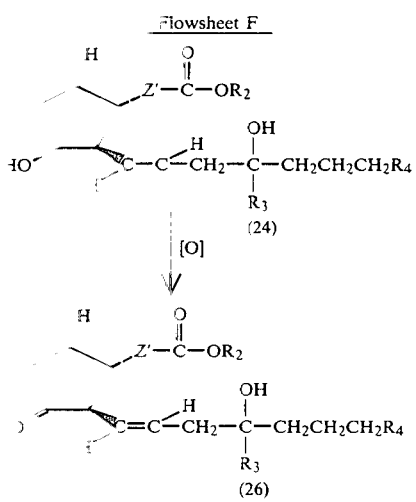

(24)

(26)

Wherein Z' is—(CH$_2$)$_n$,—(CH$_2$)$_m$ OCH—and—CH$_2$CH=CH(CH$_2$)p—and n, m and p are previously described.

In accordance with Flowsheet F when 11α-hydroxy-PGFα congeners such as (24) are treated with an oxidizing reagent such as Jones Reagent, or pyridinium chlorochromate provides a selective oxidation provides the corresponding PGD derivative (9α-hydroxy-11-keto) (26), which is isolated after chromatographic purification.

If one utilized the individual 16α-hydroxy or 16β-hydroxy PGF derivative of (24), then the corresponding 9α,16α-dihydroxy-11-oxo and 9α,16β-dihydroxy-11-oxo-prostaglandins are isolated, respectively.

The 4-hydroxycyclopentenone racemates may be resolved into their component enantiomers (28) and (29) wherein Z is as hereinabove defined by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-β-methylpentanoic acid hydrochloride (to give (27)), (R)-2-aminoxy-3,3-dimethyl-butyric acid hydrochloride, and 4-α-methylbenzyl semicarbazide. After separation of the diastereomeric derivatives, reconstitution of the keto function provides the individual 4-hydroxycyclopentenone enantiomers (28) and (29). A useful procedure for the resolution of a 4-hydroxycyclopentenone racemate via an oxime such as (27) is described in the art [R. Pappo, P. Collins and C. Jung, Tetrahedron Letters, 943 (1973)]. The resolution of the hydroxycyclopentenone (28) wherein Z is

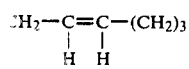

is described by Bruhn et al, Tetrahedron Letters, 235 (1976).

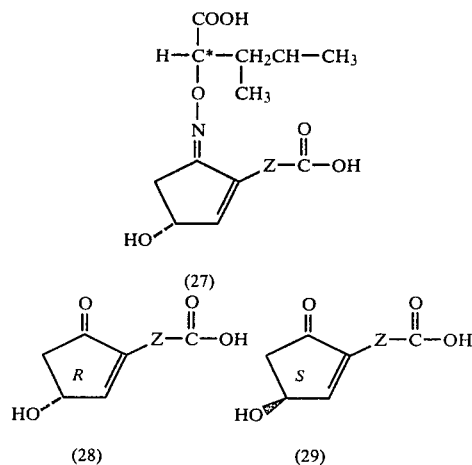

(27)

(28) (29)

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various nonsteroidal anti-inflammatory agents (e.g., indomethacin, aspirin, and phenylbutazone), bronchodilators, anti-inflammatory agents, abortifacients, agents for the induction of labor, agents for the induction of menses, fertility-controlling agents, oestrus regulators for use in animal husbandry with cattle and other domestic animals and central nervous system regulatory agents. Certain of the novel compounds of this invention possess utility as intermediates for the preparation of the other novel compounds of this invention.

The novel compounds of this invention possess the pharmacological activity described below as associated with the appropriate above-described prostaglandin types.

The known PGE, PGFα, PGFβ, PGA and PGD compounds are all potent in causing multiple biological responses even at low doses. For example, PGE$_1$, PGE$_2$, PGA$_1$ and PGA$_2$ are extremely potent in causing vasodepression and smooth muscle stimulation, and also are potent as antilipolytic agents. For example, the 11-deoxy-PGE compounds of this invention are selective in that they are at most relatively weak stimulants of smooth muscle. A further advantage of these novel compounds should be in their increased stabilities and lengthened shelf-lives.

Therefore, each of these novel prostaglandin analogs of this invention should be more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively orally, sublingually, intravaginally, buccally, or rectally, in addition to the usual intravenous, instramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

$PGE_1$, $PGE_2$, $PGE_3$, dihydro-$PGE_1$, $PGE_\alpha$, $PGF_\beta$ and PGA compounds, their esters and pharmacologically acceptable salts, are extremely potent in causing various biological responses. For that reason, these compounds are useful for pharmacological purposes. See, for example, Bergstrome, et al., Pharmacol. Rev., 20, 1 (1968), and references cited herein. A few of those biological responses are systemic arterial blood pressure lowering in the case of the PGA and PGE compounds as measured, for example, in anesthetized (sodium phenobarbital) pentolinium-treated rats with indwelling aortic and right heart cannulas; pressor activity, similarly measured, for the PGF compounds; stimulation of smooth muscle as shown, for example, by tests on strips of guinea pig ileum, rabbit duodenum, or gerbil colon; potentiation of other smooth muscle stimulants; antilipolytic activity as shown by anatagonism of epinephrine-induced mobilization of free fatty acids or inhibition of the spontaneous release of glycerol from isolated rat fat pads; inhibition of gastric secretion in the case of PGE compounds, as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen, and in the case of the PGE and PGA compounds, stimulation of epidermal proliferation and keratinization, as shown when they are applied in culture to embryonic chick and rat skin segments.

Because of these biological responses, these known prostaglandins are useful to study, prevent, control, or alleviate a wide variety of disease and undesirable physiological conditions in birds and mammals including humans, useful domestic animals, pets, and zoological specimens, and in laboratory animals, e.g., mice, rats, rabbits, and monkeys.

For example, these compounds are useful in mammals, including man, as nasal decongestants. For this purpose, the compounds are used in a dose range of about 0.1 mg to about 10 mg per ml of a pharmacologically suitable liquid vehicle or as an aerosol spray, both for topical application.

PGA, $PGF_\beta$ and PGE compounds are useful as hypotensive agents to reduce blood pressure in mammals including man. For this purpose, the $PGF_\beta$ compounds are administered by intravenous infusion at the rate of about 0.01 mg to about 40 mg per Kg of body weight per minute, or in a single dosage or multiple doses of about 25 mg to 2500 mg per Kg of body weight total per day. The PGE and PGA compounds are administered by intravenous infusion at the rate of about 0.01 to about 50 mg per Kg of body weight per minute, or in a single dose or multiple doses of about 25 to 2500 mg per Kg of body weight total per day.

The PGE, $PGF_\alpha$ and $PGF_\beta$ compounds are useful in place of oxytocin to induce labor in pregnant female animals, including humans, cows, sheep and pigs, at or near term or in pregnant animals with intrauterine death of the fetus from about 20 weeks to term. For this purpose, the PGF compound is infused intravenously at a dose of 0.01 mg to 50 mg per Kg of body weight per minute until or near the termination of the second stage of labor, i.e., expulsion of the fetus. Similarly, the PGE compound is infused intravenously at a dose of 0.01 to 50 mg per Kg of body weight per minute until or near the expulsion of the fetus. These compounds are especially useful when the female is one or more weeks postmature and natural labor has not started, or 12 to 60 hours after the membranes have ruptured and natural labor has not yet started.

The PGE, $PGF_\alpha$ and $PFG_\beta$ compounds are useful for controlling the reproductive cycle in ovulating female mammals, including humans and other animals. For that purpose, $PGF_{2\alpha}$, for example, is administered systemically at a dose level in the range of 0.01 mg to about 20 mg per Kg of body weight, advantageously during a span of time starting approximately at the time of ovulation and ending approximately at the time of menses or just prior to menses. Likewise, a PGE compound is administered in the same fashion at a dose level of 0.01 mg to about 50 mg per Kg of body weight. Additionally, expulsion of an embryo or fetus is accomplished by similar administration of the compound during the first third or the second third of the normal mammalian gestation period. Accordingly, such compounds are useful as abortifacients. They are also useful for induction of menses during approximately the first two weeks of a missed menstrual period and thus, are useful as contraceptive anti-fertility agents.

11α-hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators for example, to relieve the symptoms of paralytic ileus, to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 mg per Kg of body weight per minute until the desired effect is obtained. Subsequent doses are given by intravenous, subcutaneous, or intramuscular injection or infusion during puerperium in the range of 0.01 to 2 mg per Kg of body weight per day, the exact dose depending on the age, weight, and condition of the patient or animal.

The novel PGA, PGE and $PGF_\beta$ of this invention are also useful as bronchodilators for the treatment of asthma and chronic bronchitis. As such they may be conveniently administered by inhalation of aerosol sprays prepared in a dose range of about 10 μg to about 10 mg/ml of a pharmacologically suitable liquid vehicle. Relative to the natural prostaglandins, the PGA and PGE compounds in particular have the significant advantage of inducing prolonged effects.

The PGE and PGA compounds are also useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 mg to about 500 mg per Kg of body weight per minute, or in a total daily dose by injection or infusion in the range of about 0.1 to about 20 mg per Kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE and PGA compounds also stimulate epidermal proliferation and keratinization, and in such a capacity are useful to promote and accelerate healing of skin which has been damaged, for example, by burns, wounds, abrasions or surgery. The PGA compounds are particularly useful in speeding the adherence and growth of skin autografts, especially small, deep (Davies) grafts which are intended to cover skinless areas by subsequent outward growth rather than initially, and in retarding rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion cream, or ointment in combination with the usual pharmaceutically acceptable diluents. In some instances, when there is substantial fluid loss as in the case of extensive burns or skin loss due to other causes, systemic administration of PGE is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Illustrative of a wet dressing for topical application to second and/or third degree burns of skin area 5 to 25 square centimeters is the use of an isotonic aqueous solution containing one to 500 mg/ml of the PGA compound or several times that concentration of the PGE compound. Especially for topical use, these prostaglandins are useful in combination with antibiotics such as gentamycin, neomycin, polymyxin B, bacitracin, spectinomycin, and oxytetracycline; with other antibacterials such as mafenide hydrochloride, sulfadiazine, furazolium chloride, and nitrofurazone; and with corticoid steroids, such as hydrocortisone, prednisolone, methylprednisolone, and fluoroprednisolone; each of those being used in the combination at the usual concentration suitable for its use alone.

The PGA compounds are derivatives and salts thereof increase the flow of blood in the mammalian kidney, thereby increasing the volume and electrolyte content of the urine. For that reason, PGA compounds are useful in managing cases of renal disfunction, especially in cases of severely impaired renal blood flow, for example, the hepatorena syndrome and early kidney transplant rejection. In case of excessive or inappropriate antidiuretic hormone ADH vasopressin secretion, the diuretic effect of these compounds is even greater. In anephretic states, the vasopressin action of these compounds is especially useful.

The PGE compounds of this invention are also useful as topical vasodilators.

The PGE$_1$ compounds of this invention are useful whenever it is desired to inhibit platelet aggregation, to reduce the adhesive character of platelets, and to remove or prevent the formation of thrombi in mammals including man, rabbits, and rats. For example, these compounds are useful to treat and prevent myocardial infarcts and post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg per Kg of body weight per day are used, the exact dose depending on the age, weight, and condition of the patient or animal, and on the frequency and route of administration.

It is well known that platelet aggregation inhibitors may be useful as anti-thrombotic drugs. Inhibition of platelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervals from animals given inhibitors by an oral or parenteral route.

The PGE compounds of the present invention exhibit the ability to inhibit playelet aggregation in vitro when tested by the following procedure.

Human protein rich plasma is incubated with modified Tyrode's solution in a proportion of 40-50% human protein rich plasma. The test compounds are added at varying concentrations and after 5 minutes incubation, an aggregating agent such as adenosine diphosphate or collagen is added. The change in optical density (light transmission) is monitored by eye and inhbition is recorded as a (−) or lack of inhibition is recorded as a (+). Test compounds are considered active if they inhibit adenosine diphosphate or collagen induced aggregation at a concentration of 0.025 mg/ml or less within 5-10 minutes.

The PGE compounds of this invention also have bronchodilator activity as determined in a test using dogs anesthetized, artificially ventilated and submitted to a continuous respiratory spasm induced by pilocarpine.

Mongrel dogs of either sex weighing between 5 and 10 kg are used. They are premedicated with morphine HCl by subcutaneous injection at 1.5 mg/Kg. An intravenous perfusion of 5% (W/V) chloralose is started ½ hour after the morphine injection in such a way that 60 mg/Kg are administered within 15 minutes. After completion, a continuous perfusion of 10 mg/Kg/hour is maintained throughout the experiment. The dogs are artificially ventilated by means of a Starling pump at a rate of 20 breaths/minute. The volume is adjusted according to the weight of the animal. [Kleinman and Radford, J. Appl. Physiol., 19, 360 (1964)]. All the measurements are made with the dogs positioned supine in a heated, V-shaped table. Curarization is obtained by succinylcholine chloride using a starting injection of 3 mg/Kg lasting 3 minutes, followed by a continuous perfusion of 0.1 mg/Kg/minute.

The respiratory spasm is induced by a starting injection of 400 µg/Kg of pilocarpine HCl lasting 5 minutes. An increase or decrease in the dose of pilocarpine HCl may occur as a function of the observed effect on the airway's resistance. A 15 minute delay is observed before the start of a continuous perfusion of pilocarpine HCl at a dose of 4 μg/Kg/minute to maintain a constant spasm during the test.

A metallic cannula is inserted and fixed, after tracheotomy, into the upper part of the trachea. The two cephalic veins and the two femoral veins are catheterized to inject the various agents. The femoral artery is catheterized to measure the systemic blood pressure. An esophageal balloon (11 cm×2.5 cm) is inserted into the lower third of the oseophagus to measure the endothoracic pressure. The measurement of air flow is made with a Fleish pneumotachograph connected to the tracheal tube.

The transpulmonary pressure is measured as follows: The tracheal cannula is equipped with a stainless steel axial tube (1.5 mm) which is closed at its distal end and projected 2.5 cm beyond the end of the cannula. Three holes with a diameter of one mm are pierced on this latter segment. This tube, which is used to measure the tracheal pressure, is connected to one end of the two chambers of a Sanborn 267 B/C differential transducer. The other chamber is connected to the esophageal ballon by means of a polyethylene catheter of the same length and characteristics as the balloon's.

The airflow is measured from the Fleish pneumotachograph by means of a Sanborn 270 differential transducer.

The tidal volume is obtained by electronic integration of the flow signal using an R.C. integrator.

The systemic and pulmonary blood pressures are gauged by means of a Sanborn 267 B/C or 1280B pressure transducer.

An electrocardiogram is taken in lead 2. Its use is to monitor a cardiac rate-meter.

All these parameters are recorded on a Sanborn polygraph. The transpulmonary pressure and the tidal volume are also displayed as rectangular coordinates on an oscilloscope.

The airway's resistance, expressed in cm of water/liter/second, is measured by subtracting from the electrical equivalent of the transpulmonary pressure, a voltage proportional to the flow so as to synchronize the pressure and volume signals on the oscilloscope [Mead and Whittenberger, J. Appl. Physiol., 5,779 (1953)].

The value of the pulmonary elastance, expressed in cm of water/liter, is obtained by means of the same principle, i.e., an electrical signal proportioned to the volume is subtracted from the transpulmonary pressure signal, in order to optimize the pressure-flow loop on the oscilloscope.

The details of this method are described by Lulling, et al. [Med. Pharmacol. Exp., 16, 481 (1967)].

The computing operations are carried out with an analogical computer which allows the direct reading, cycle to cycle, of the values of resistance and elastance.

The test compounds are administered by an Aerosol ® route. The micronebulizer of a Bird Mark 7 respirator is fitted on the metallic cannula just after the pneumotachograph. The "puff" of the test compound, in Aerosol ® is driven by a 2 Kg/cm$_2$ pressure, allowed into the micronebulizer just during one inspiration cycle. The microenbulizer is fitted on the respiratory tube only during the "puff." It is weighed just before and just after administration to determine the amount of test compound administered. Approximately 50 mg of the solution is administered to each dog. In accordance with the Pilocarpine Assay described herein, the compounds of this invention should exhibit bronchodilator activity.

The bronchodilator activity for representative compounds of this invention was determined in Guinea-Pigs against bronchospasms elicited by intravenous injections of serotonin, histamine, and acetylcholine, by the Konzett procedure, the details of which are discussed by J. Lulling, P Lievens, F. El Sayed and J. Prignot, Arzeimittel-Forschung 18, 995 (1968).

In the table which follows, bronchodilator activity for representative compounds of the invention against spasmogenic agents serotonin, histamine, and acetylcholine is expressed as an $ED_{50}$ determined from the results obtained with three logarithmic cumulative intravenous doses.

| | KONZETT DATA | | |
| --- | --- | --- | --- |
| | $ED_{50}$ mg/kg | | |
| COMPOUND | SEROTONIN | HISTAMINE | ACETYLCHOLINE |
| dl 15-deoxy-16-hydroxy-16-allenyl-PGE$_1$ | $1.05 \times 10^{-3}$ | $1.0 \times 10^{-3}$ | $1.2 \times 10^{-3}$ |
| dl 15-deoxy-16-hydroxy-16-allenyl-PGE$_2$ | $1.4 \times 10^{-3}$ | $1.0 \times 10^{-3}$ | $1.2 \times 10^{-3}$ |

REFERENCE EXAMPLE 1

1,2-Octadien-4-one

To a stirred solution of 0.50 moles of propargylmagnesium bromide in 340 ml. of ether at −78° C. is added a solution of 65.2 g. (0.50 moles) of the ethyl valerate in 100 ml. of ether during 60 minutes. The solution is stirred at −78° C. for 30 minutes and then hydrolyzed by pouring onto a mixture of ice and ether. The ether layer is washed with brine, treated with hydroquinone, dried over magnesium sulfate, and concentrated.

To a stirred, ice-cold solution of the liquid concentrate (94 g.) in 1200 ml. of tetrahydrofuran is added 60 ml. of 10% potassium carbonate solution. The resulting mixture is stirred at 0° C. for 2 hours, treated with 15 ml. of 4 N hydrochloric acid, and diluted with ether. The organic layer is washed with brine, dried over magnesium sulfate, treated with hydroquinone and concentrated. The product is distilled to provide the title compound as a colorless liquid, b.p. ca 80° C. (15 mm.).

REFERENCE EXAMPLE 2

4-Hydroxy-4-propadienyl-1-octyne

To a stirred solution of 125 mmol. of propargylmagnesium bromide in 85 ml. of ether at −20° C. is added a solution of 11.7 g. (95 mmol.) of 1,2-octadien-4-one in 30 ml. of ether during 30 minutes. After the addition, the solution is stirred at 25° C. overnight, cooled to 0° C., and treated dropwise with 18 ml. of saturated ammonium chloride solution. The mixture is filtered, and the filtrate is washed with brine, dried over magnesium sulfate, and concentrated. The product is distilled from anhydrous potassium carbonate to provide the title compound as a colorless liquid, b.p. 84°-87° C. (7 mm.).

REFERENCE EXAMPLE 3

4-Propadienyl-4-trimethylsilyloxy-1-octyne

To a stirred, ice-cold solution of 10.85 g. (66.1 mmol.) of 4-hydroxy-4-propadienyl-1-octyne and 13.2 g. (194 mmol.) of imidazole in 50 ml. of dimethylformamide at 0° C. is added 9.5 ml. of chlorotrimethylsilane. The solution is kept at 0° C. for 70 hours and diluted with petroleum ether. The resulting mixture is shaken with water at 0° C. The organic layer is washed with water and brine, dried over magnesium sulfate and concentrated to give the title compound as a liquid.

REFERENCE EXAMPLE 4

1-Iodo-4-propadienyl-4-trimethylsilyloxy-trans-octene

To a stirred solution of 2.36 g. (10 mmol.) of 4-propadienyl-4-trimethylsilyloxy-1-octyne in 5 ml. of glyme is added a solution of 11 mmol. of bis-(3-methyl-2-butyl)-borane in 15 ml. of glyme at 0° C. The mixture is stirred at 25° C. for 90 minutes, cooled to 0° C., and treated portionwise with 3.0 g. of triethylamine oxide. The hydrofuran and 10 ml. of water, and the resulting mixture is stirred at room temperature for 1.5 hours. The solution is partitioned with ethyl acetate and brine and the ethyl acetate layer is washed with brine, dried over magnesium sulfate and concentrated.

REFERENCE EXAMPLE 6

Treatment of the ethyl esters of Table A with propargyl magnesium bromide by the procedure of Reference Example 1 followed by treatment with propargyl magnesium bromide by the procedure of Reference Example 2 followed by silyl ether formation by the procedure of Reference Example 3 followed by iodovinylation by the procedure of Reference Example 4 is productive of the iodoalkenes and intermediates listed in Table A.

TABLE A

| STARTING ESTER | DIENEONE | HYDROXYALKYNE | SILYLOXYALKYNE | IODOALKENE |
| --- | --- | --- | --- | --- |
| ethyl hexanoate | 1,2-nonadien-4-one | 4-hydroxy-4-propadienyl-1-nonyne | 4-propadienyl-4-trimethylsilyloxy-1-nonyne | 1-iodo-4-propadienyl-4-trimethylsilyloxy-trans-1-nonene |
| ethyl heptanoate | 1,2-decadien-4-one | 4-hydroxy-4-propadienyl-1-decyne | 4-propadienyl-4-trimethylsilyloxy-1-decyne | 1-iodo-4-propadienyl-4-trimethylsilyloxy-trans-1-decene |
| ethyl butyrate | 1,2-heptadien-4-one | 4-hydroxy-4-propadienyl-1-heptyne | 4-propadienyl-4-trimethylsilyloxy-1-heptyne | 1-iodo-4-propadienyl-4-trimethylsilyloxy-trans-1-heptene |
| ethyl-4-chloro-butyrate | 7-chloro-1,2-heptadiene-4-one | 7-chloro-4-hydroxy-4-propadienyl-1-heptyne | 7-chloro-4-propadienyl-4-trimethylsilyloxy-1-heptyne | 1-iodo-7-chloro-4-propadienyl-4-trimethylsilyloxy-trans-1-heptyne | stirred mixture is maintained at 25°–30° C. for 45 minutes, diluted with 20 ml. of tetrahydrofuran and poured into 100 ml. of ice-cold 15% sodium hydroxide solution, followed immediately with a solution of 8.0 g. of iodine in 20 ml. of tetrahydrofuran. The mixture is stirred at ambient temperature for 30 minutes and then extracted with ether. The extract is washed successively with water, sodium thiosulfate solution and brine; dried over magnesium sulfate; and filtered. The residue obtained after solvent evaporation is subjected to chromatography on silica gel with heptane solvent to afford the title compound as a liquid.

REFERENCE EXAMPLE 5

9-Oxo-11α,16-dihydroxy-16-propadienyl-5-cis,13-trans-prostadienoic acid

To a stirred solution of 2.19 g. (6.0 mmol.) of 1-iodo-4-propadienyl-4-trimethylsilyloxy-trans-1-octene in 25 ml. of ether at −78° C. is added 5.2 ml. of 2.3 M t-butyl-lithium in pentane during 10 minutes. The resulting solution is stirred at −78° C. for 1.5 hours, warmed to −50° C. during 10 minutes, and then recooled to −78° C. To the stirred solution is added a solution prepared from 0.78 g. of pentynyl-copper, 3.0 ml. of tri-n-butyl-phosphine, and 3 ml. of ether during 10 minutes. The resulting solution is stirred at −78° C. for 60 minutes and then treated during 5 minutes with a solution of 1.84 g. (5.0 mmol.) of 2-(6-trimethylsilyloxycarbonyl-2'-cis-hexenyl)-4-trimethylsilyloxycyclopent-2-en-1-one in 5 ml. of ether. The resulting solution is stirred at −40° C. for 1.5 hours, recooled to −78° C. and treated with a solution of 0.72 ml. of glacial acetic acid in 10 ml. of ether. The mixture is diluted with ether and treated with cold ammonium chloride solution. The ether phase is washed with water and brine, dried over magnesium sulfate and concentrated.

The resulting liquid is treated with a solution prepared from 40 ml. of glacial acetic acid, 20 ml. of tetrahydrofuran and 10 ml. of water, and the resulting mixture is stirred at room temperature for 1.5 hours. The solution is partitioned with ethyl acetate and brine and the ethyl acetate layer is washed with brine, dried over magnesium sulfate and concentrated.

REFERENCE EXAMPLE 7

PREPARATION OF 9α, 11α, 16-TRIHYDROXY-16-ALLENYL-5-CIS,13-TRANS-PROSTADIENOIC ACID.

To a stirred solution solution of 9-oxo-11α, 16-dihydroxy-16-allenyl-5-cis, 13-trans-prostadienoic acid in tetrahydrofuran (THF) at −78° C. is added an excess of a 0.5 M solution of lithium perhydro-9 -boraphenalyl hydride in THF. After 30 min. at −78° C., the solution is warmed to 0° C. and treated with water. This mixture is partitioned with ether-potassium carbonate solutions. The aqueous phase is carefully acidified with hydrochloric acid, saturated with NaCl, and extracted with ethyl acetate. The organic extract is washed with brine, dried with magnesium sulfate, and concentrated in vacuo.

The residue is subjected to silica-gel dry column chromatography to provide 9α,11α,16-trihydroxy 16-allenyl-5-cis, 13-trans prostandienoic acid which may be separated into the individual 16α- and 16β-hydroxy isomers by HPLC techniques.

REFERENCE EXAMPLE 8

PREPARATION AND SEPARATION OF 9α,11α,16-TRIHYDROXY-16-ALLENYL-5-CIS, 13-TRANS-PROSTADIENOIC ACID AND 9β,11α,16-TRIHYDROXY-16-ALLENYL-5-CIS, 13-TRANS PROSTADIENOIC ACID.

To a stirred, ice-cold solution of 9-oxo-11α, 16-dihydroxy-16-allenyl-5-cis, 13-trans-prostadienoic acid in ethanol is added excess sodium borohydride in small portions during 1 minute. The mixture is stirred at 0° C. for 5 minutes and at ambient temperature for 1.5 hours. The bulk of the ethanol is evaporated in vacuo at room temperature and the residue is partitioned with cold, very dilute, hydrochloric acid and ethyl acetate. The organic phase is evaporated and washed with water and brine and dried over magnesium sulfate and concentrated in vacuo.

The residue is subjected to silica-gel chromatography to give: first eluted - 9α,11α,16-trihydroxy-16-allenyl-5-cis, 13-trans-prostadienoic acid followed by 9β,11α,16-trihydroxy-16-allenyl-5-cis, 13-trans-prostadienoic acid.

If one starts with the individual 16α or 16β-hydroxy isomer, then the corresponding products will also be 16α or 16β-hydroxy, respectively.

REFERENCE EXAMPLE 9

PREPARATION OF 9-OXO-16-HYDROXY-16-ALLENYL-5-CIS, 10, 13-TRANSPROSTATRIENOTIC ACID 9-oxo-11α,16-dihydroxy-16-allenyl-5-cis, 13-trans-prostadienoic acid is dissolved in a 1:1 tetrahydrofuran-water mixture containing 0.5 N HCl and allowed to stand at ambient temperature under argon for 72 hours. The solution is treated with brine and extracted with ether. The extract is washed with brine, dried over magnesium sulfate, and concentrated in vacuo to an oil. This residue is purified by dry column chromatography to give 9-oxo-16-hydroxy-16-allenyl-5-cis,10, 13-trans-prostatrienoic acid. If one utilizes the individual 16α or 16β isomer, the product obtained is the 16α or 16β-epimer respectively.

REFERENCE EXAMPLE 10

PREPARATION OF 9α,16-DIHYDROXY-11-OXO-16-ALLENYL-5-CIS, 13-TRANS-PROSTADIENOIC ACID

To a solution of 9α,11α, 16-trihydroxy-16-allenyl-5-cis, 13-trans-prostadienoic acid in acetone (12 ml/g.) at −35° C. is added, dropwise with stirring, one equivalent of Jones Reagent (2.67 g CrO₃ and 2.3 ml of conc. H₂SO₄ diluted to 10 ml with water). After 15 min isopropanol is added, followed by water. The mixture is poured into water, saturated with NaCl, extracted with ethyl acetate, dried over magnesium sulfate, and concentrated in vacuo to an oil.

This oil is chromatographed on a dry column of silica-gel using ethyl acetate/heptane mixtures containing 1% acetic acid, to provide the product above.

If one starts with ether of the individual 16α- or 16β-hydroxy isomers, one isolates the 16α- or 16β-hydroxyl isomer, respectively.

Although in Tables I and II which follow, the product listed in the dl-racemic product, when the cyclopentenone employed is the optically active cyclopentenone (such as 11 supra) the application of HPLC, column or thin layer chromatography will provide the individual nat. 16α and nat. 16β prostaglandins. The cyclopentenones employed are those which are listed below in Table B.

TABLE B

CYCLOPENTENONES

A. 2-(5-Carbotrimethylsiloxypent-2-cis-enyl-4-trimethylsiloxycyclopent-2-en-1-one
B. 2-(6-Carbotrimethylsiloxyhex-2-cis-enyl)-4-trimethylsiloxycyclopent-2-en-1-one
C. 2-(7-Carbotrimethylsiloxyhept-2-cis-enyl-4-trimethylsiloxycyclopent-2-en-1-one
D. 2-(5-Carbotrimethylsiloxypentyl)-4-trimethylsiloxycyclopent-2-en-1-one
E. 2-(6-Carbotrimethylsiloxyhexyl)-4-trimethylsiloxycyclopent-2-en-1-one
F. 2-(7-Carbotrimethylsiloxyheptyl)-4-trimethylsiloxycyclopent-2-en-1-one
G. 2-(6-Carbotrimethylsiloxy-5-thia-hexyl)-4-trimethylsiloxycyclopent-2-en-1-one
H. 2-(6-Carbotrimethylsiloxy-5-oxa-hexyl)-4-trimethylsiloxycyclopent-2-en-1-one
I. 2-(6-Carbotrimethylsiloxyhex-2-cis-enyl)-4R-trimethylsiloxycyclopent-2-en-1-one
J. 2-6(-Carbotrimethylsiloxyhexyl)-4R-trimethylsiloxycyclopent-2-en-1-one
K. 2-(5-Carboethoxypent-2-cis-enyl)-cyclopent-2-en-1-one
L. 2-(6-Carboethoxyhex-2-cis-enyl)-cyclopent-2-en-1-one
M. 2-(7-Carboethoxyhept-2-cis-enyl)-cyclopent-2-en-1-one
N. 2-(5-Carboethoxypentyl)cyclopent-2-en-1-one
O. 2-(6-Carboethoxyhexyl)cyclopent-2-en-1-one
P. 2-(7-Carboethoxyheptyl)cyclopent-2-en-1-one
Q. 2-(6-Carboethoxy-5-thiahexyl)cyclopent-2-en-1-one
R. 2-(6-Carboethoxy-5-oxahexyl)cyclopent-2-en-1-one

TABLE I

Treatment of the appropriate cyclopentenones of Table B with the lithiocuprates derived from the vinyliodides of Reference Examples 4 and 6 by the procedure of Reference Example 5 is productive of the PGE₁ derivatives of Examples 1–44 of Table I.

| EXAMPLE | VINYL IODIDE | CYCLOPENTENONE | PRODUCT PROSTAGLANDIN OF THE PGE₁ SERIES |
|---|---|---|---|
| 1 | 1-trans-iodo-4-allenyl-4-trimethylsiloxy-1-heptene | 2-(5-carbotrimethylsiloxypentyl)-4-trimethylsiloxycyclopent-2-en-1-one | dl-11α,16-dihydroxy-9-oxo-16-allenyl-20-nor-2-nor-13-trans prostenoic acid |
| 2 | 1-trans-iodo-4-allenyl-4-trimethylsiloxy-1-octene | 2-(5-carbotrimethylsiloxypentyl)-4-trimethylsiloxycyclopent-2-en-1-one | dl-11α,16-dihydroxy-9-oxo-16-allenyl-2-nor-13-trans prostenoic acid |
| 3 | 1-trans-iodo-4-allenyl-4-trimethylsiloxy-1-nonene | 2-(5-carbotrimethylsiloxypentyl)-4-trimethylsiloxycyclopent-2-en-1-one | dl-11α,16-dihydroxy-9-oxo-16-allenyl-20-methyl-2-nor-13-trans prostenoic acid |
| 4 | 1-trans-iodo-4-allenyl-4-trimethylsiloxy-1-decene | 2-(5-carbotrimethylsiloxypentyl)-4-trimethylsiloxycyclopent-2-en-1-one | dl-11α,16-dihydroxy-9-oxo-16-allenyl-20-ethyl-2-nor-13-trans prostenoic aid |
| 5 | 1-trans-iodo-4-allenyl-4-trimethylsiloxy-1-heptene | 2-(6-carbotrimethylsiloxyhexyl)-4-trimethylsiloxycyclopent-2-en-1-one | dl-11α,16-dihydroxy-9-oxo-16-allenyl-20-nor-13-trans prostenoic acid |
| 6 | 1-trans-iodo-4-allenyl-4-trimethylsiloxy-1-octene | 2-(6-carbotrimethylsiloxyhexyl)-4-trimethylsiloxycyclopent-2-en-1-one | dl-11α,16-dihydroxy-9-oxo-16-allenyl-13-trans prostanoic acid |
| 7 | 1-trans-iodo-4-allenyl-4-trimethylsiloxy-1-nonene | 2-(6-carbotrimethylsiloxyhexyl)-4-trimethylsiloxycyclopent-2-en-1-one | dl-11α,16-dihydroxy-9-oxo-16-allenyl-20-methyl-13-trans prostenoic acid |
| 8 | 1-trans-iodo-4-allenyl-4-trimethylsiloxy-1-decene | 2-(6-carbotrimethylsiloxyhexyl)-4-trimethylsiloxycyclopent-2-en-1-one | dl-11α,16-dihydroxy-9-oxo-16-allenyl-20-ethyl-13-trans prostenoic acid |
| 9 | 1-trans-iodo-4-allenyl-4-trimethylsiloxy-1-heptene | 2-(7-carbotrimethylsiloxyheptyl)-4-trimethylsiloxycyclopent-2-en-1-one | dl-11α,16-dihydroxy-9-oxo-16-allenyl-20-nor-2-homo-13-trans prostenoic acid |

-continued

| EXAMPLE | VINYL IODIDE | CYCLOPENTENONE | PRODUCT |
|---|---|---|---|
| 10 | trans-iodo-4-allenyl--trimethylsiloxy-1-octene | 2-(7-carbotrimethylsiloxyheptyl)-4-trimethylsiloxycyclopent-2-en-1-one | dl-11α,16-dihydroxy-9-oxo-16-allenyl-2-homo-13-trans prostenoic acid |
| 11 | trans-iodo-4-allenyl--trimethylsiloxy-1-nonene | 2-(7-carbotrimethylsiloxyheptyl)-4-trimethylsiloxycyclopent-2-en-1-one | dl-11α,16-dihydroxy-9-oxo-16-allenyl-20-methyl-2-homo-13-trans prostenoic acid |
| 12 | trans-iodo-4-allenyl--trimethylsiloxy-1-decene | 2-(7-carbotrimethylsiloxyheptyl)-4-trimethylsiloxycyclopent-2-en-1-one | dl-11α,16-dihydroxy-9-oxo-16-allenyl-20-ethyl-2-homo-13-trans prostenoic acid |
| 13 | trans-iodo-4-allenyl--trimethylsiloxy-1-heptene | 2-(6-carbotrimethylsiloxy-5-thiahexyl)-4-trimethylsiloxycyclopent-2-en-1-one | dl-11α,16-dihydroxy-9-oxo-16-allenyl-20-nor-3-thia-13-trans prostenoic acid |
| 14 | trans-iodo-4-allenyl--trimethylsiloxy-1-octene | 2-(6-carbotrimethylsiloxy-5-thiahexyl)-4-trimethylsiloxycyclopent-2-en-1-one | dl-11α,16-dihydroxy-9-oxo-16-allenyl-3-thia-13-trans prostenoic acid |
| 15 | trans-iodo-4-allenyl--trimethylsiloxy-1-nonene | 2-(6-carbotrimethylsiloxy-5-thiahexyl)-4-trimethylsiloxycyclopent-2-en-1-one | dl-11α,16-dihydroxy-9-oxo-16-allenyl-20-methyl-3-thia-13-trans prostenoic acid |
| 16 | trans-iodo-4-allenyl--trimethylsiloxy-1-decene | 2-(6-carbotrimethysiloxy-5-thiahexyl)-4-trimethylsiloxycyclopent-2-en-1-one | dl-11α,16-dihydroxy-9-oxo-16-allenyl-20-ethyl-3-thia-13-trans prostenoic acid |
| 17 | trans-iodo-4-allenyl--trimethylsiloxy-1-heptene | 2-(6-carbotrimethylsiloxy-5-oxahexyl)-4-trimethylsiloxycyclopent-2-en-1-one | dl-11α,16-dihydroxy-9-oxo-16-allenyl-20-nor-3-oxa-13-trans prostenoic acid |
| 18 | trans-iodo-4-allenyl--trimethylsiloxy-1-octene | 2-(6-carbotrimethylsiloxy-5-oxahexyl)-4-trimethylsiloxycyclopent-2-en-1-one | dl-11α,16-dihydroxy-9-oxo-16-allenyl-3-oxa-13-trans prostenoic acid |
| 19 | trans-iodo-4-allenyl--trimethylsiloxy-1-nonene | 2-(6-carbotrimethylsiloxy-5-oxahexyl)-4-trimethylsiloxycyclopent-2-en-1-one | dl-11α,16-dihydroxy-9-oxo-16-allenyl-20-methyl-3-oxa-13-trans prostenoic acid |
| 20 | trans-iodo-4-allenyl--trimethylsiloxy-1-decene | 2-(6-carbotrimethylsiloxy-5-oxahexyl)-4-trimethylsiloxycyclopent-2-en-1-one | dl-11α,16-dihydroxy-9-oxo-16-allenyl-20-ethyl-3-oxa-13-trans prostenoic acid |
| 21 | trans-iodo-4-allenyl--trimethylsiloxy-1-heptene | 2-(6-carbotrimethylsiloxyhexyl)-4R-trimethylsiloxycyclopent-2-en-1-one | nat-11α,16-dihydroxy-9-oxo-16-allenyl-20-nor-13-trans prostenoic acid |
| 22 | trans-iodo-4-allenyl--trimethylsiloxy-1-octene | 2-(6-carbotrimethylsiloxyhexyl)-4R-trimethylsiloxycyclopent-2-en-1-one | nat-11α,16-dihydroxy-9-oxo-16-allenyl-13-trans prostenoic acid |
| 23 | trans-iodo-4-allenyl--trimethylsiloxy-1-nonene | 2-(6-carbotrimethylsiloxyhexyl)-4R-trimethylsiloxycyclopent-2-en-1-one | nat-11α,16-dihydroxy-9-oxo-16-allenyl-20-methyl-13-trans prostenoic acid |
| 24 | trans-iodo-4-allenyl--trimethylsiloxy-1-decene | 2-(6-carbotrimethylsiloxyhexyl)-4R-trimethylsiloxycyclopent-2-en-1-one | nat-11α, 16-dihydroxy-9-oxo-16-allenyl-20-ethyl-13-trans prostenoic acid |

| EXAMPLE | VINYL IODIDE | CYCLOPENTENONE | PRODUCT PROSTAGLANDIN OF THE 11-DEOXY PGE₁ SERIES |
|---|---|---|---|
| 25 | trans-iodo-4-allenyl--trimethylsiloxy-1-heptene | 2-(5-carboethoxypentyl)cyclopent-2-en-1-one | dl-16-hydroxy-9-oxo-16-allenyl-20-nor-2-nor-13-trans prostenoic acid |
| 26 | trans-iodo-4-allenyl--trimethylsiloxy-1-octene | 2-(5-carboethoxypentyl)cyclopent-2-en-1-one | dl-16-hydroxy-9-oxo-16-allenyl-2-nor-13-trans prostenoic acid |
| 27 | trans-iodo-4-allenyl--trimethylsiloxy-1-nonene | 2-(5-carboethoxypentyl)cyclopent-2-en-1-one | dl-16-hydroxy-9-oxo-16-allenyl-20-methyl-2-nor-13-trans prostenoic acid |
| 28 | trans-iodo-4-allenyl--trimethylsiloxy-1-decene | 2-(5-carboethoxypentyl)cyclopent-2-en-1-one | dl-16-hydroxy-9-oxo-16-allenyl-20-ethyl-2-nor-13-trans prostenoic acid |
| 29 | trans-iodo-4-allenyl--trimethylsiloxy-1-heptene | 2-(6-carboethoxyhexyl)cyclopent-2-en-1-one | dl-16-hydroxy-9-oxo-16-allenyl-20-nor-13-trans prostenoic acid |
| 30 | trans-iodo-4-allenyl--trimethylsiloxy-1-octene | 2-(6-carboethoxyhexyl)cyclopent-2-en-1-one | dl-16-hydroxy-9-oxo-16-allenyl-13-trans prostenoic acid |
| 31 | trans-iodo-4-allenyl--trimethylsiloxy-1-nonene | 2-(6-carboethoxyhexyl)cyclopent-2-en-1-one | dl-16-hydroxy-9-oxo-16-allenyl-20-methyl-13-trans prostenoic acid |
| 32 | trans-iodo-4-allenyl--trimethylsiloxy-1-decene | 2-(6-carboethoxyhexyl)cyclopent-2-en-1-one | dl-16-hydroxy-9-oxo-16-allenyl-20-ethyl-13-trans prostenoic acid |
| 33 | trans-iodo-4-allenyl--trimethylsiloxy-1-heptene | 2-(7-carboethoxyheptyl)cyclopent-2-en-1-one | dl-16-hydroxy-9-oxo-16-allenyl-20-nor-2-homo-13-trans prostenoic acid |
| 34 | trans-iodo-4-allenyl--trimethylsiloxy-1-octene | 2-(7-carboethoxyheptyl)cyclopent-2-en-1-one | dl-16-hydroxy-9-oxo-16-allenyl-2-homo-13-trans prostenoic acid |
| 35 | trans-iodo-4-allenyl--trimethylsiloxy-1-nonene | 2-(7-carboethoxyheptyl)cyclopent-2-en-1-one | dl-16-hydroxy-9-oxo-16-allenyl-20-methyl-2-homo-13-trans prostenoic acid |
| 36 | trans-iodo-4-allenyl--trimethylsiloxy-1-decene | 2-(7-carboethoxyheptyl)cyclopent-2-en-1-one | dl-16-hydroxy-9-oxo-16-allenyl-20-ethyl-2-homo-13-trans prostenoic acid |
| 37 | trans-iodo-4-allenyl--trimethylsiloxy-1-heptene | 2-(6-carboethoxy-5-thiahexyl)cyclopent-2-en-1-one | dl-16-hydroxy-9-oxo-16-allenyl-20-nor-3-thia-13-trans prostenoic acid |
| 38 | trans-iodo-4-allenyl--trimethylsiloxy-1-octene | 2-(6-carboethoxy-5-thiahexyl)cyclopent-2-en-1-one | dl-16-hydroxy-9-oxo-16-allenyl-3-thia-13-trans prostenoic acid |
| 39 | trans-iodo-4-allenyl--trimethylsiloxy-1-nonene | 2-(6-carboethoxy-5-thiahexyl)cyclopent-2-en-1-one | dl-16-hydroxy-9-oxo-16-allenyl-20-methyl-3-thia-13-trans prostenoic acid |
| 40 | trans-iodo-4-allenyl--trimethylsiloxy-1-decene | 2-(6-carboethoxy-5-thiahexyl)cyclopent-2-en-1-one | dl-16-hydroxy-9-oxo-16-allenyl-20-ethyl-3-thia-13-trans prostenoic acid |
| 41 | trans-iodo-4-allenyl--trimethylsiloxy-1-heptene | 2-(6-carboethoxy-5-oxahexyl)cyclopent-2-en-1-one | dl-16-hydroxy-9-oxo-16-allenyl-20-nor-3-oxa-13-trans prostenoic acid |
| 42 | trans-iodo-4-allenyl--trimethylsiloxy-1-octene | 2-(6-carboethoxy-5-oxahexyl)cyclopent-2-en-1-one | dl-16-hydroxy-9-oxo-16-allenyl-3-oxa-13-trans prostenoic acid |
| 43 | trans-iodo-4-allenyl--trimethylsiloxy-1-nonene | 2-(6-carboethoxy-5-oxahexyl)cyclopent-2-en-1-one | dl-16-hydroxy-9-oxo-16-allenyl-20-methyl-3-oxa-13-trans prostenoic acid |
| 44 | trans-iodo-4-allenyl--trimethylsiloxy-1-decene | 2-(6-carboethoxy-5-oxahexyl)cyclopent-2-en-1-one | dl-16-hydroxy-9-oxo-16-allenyl-20-ethyl-3-oxa-13-trans prostenoic acid |

TABLE I (Continued)

Treatment of the PGE₁ derivatives of Examples of Table I with lithium perhydro-9β-boraphenalyl hydride by the procedure of Reference Example 7 is productive of the PGF₁ and derivatives of Examples 45–88 of Table I.

| EXAMPLE | STARTING PROSTAGLANDIN OF THE PGE SERIES | PRODUCT PROSTAGLANDIN OF THE PGF1α SERIES |
|---|---|---|
| 45 | dl-11α,16-dihydroxy-9-oxo-16-allenyl-20-nor-2-nor-13-trans prostenoic acid | dl-9α,11α,16-trihydroxy-16-allenyl-20-nor-2-nor-13-trans prostenoic acid |
| 46 | dl-11α,16-dihydroxy-9-oxo-16-allenyl-2-nor-13-trans prostenoic acid | dl-9α,11α,16-trihydroxy-16-allenyl-2-nor-13-trans prostenoic acid |
| 47 | dl-11α,16-dihydroxy-9-oxo-16-allenyl-20-methyl-2-nor-13-trans prostenoic acid | dl-9α,11α,16-trihydroxy-16-allenyl-20-methyl-2-nor-13-trans prostenoic acid |
| 48 | dl-11,16-dihydroxy-9-oxo-16-allenyl-20-ethyl-2-nor-13-trans prostenoic acid | dl-9,11α,16-trihydroxy-16-allenyl-20-ethyl-2-nor-13-trans prostenoic acid |
| 49 | dl-11α,16-dihydroxy-9-oxo-16-allenyl-20-nor-13-trans prostenoic acid | dl-9α,11α,16-trihydroxy-16-allenyl-20-nor-13-trans prostenoic acid |
| 50 | dl-11α,16-dihydroxy-9-oxo-16-allenyl-13-trans prostenoic acid | dl-9α,11α,16-trihydroxy-16-allenyl-13-trans prostenoic acid |
| 51 | dl-11α,16-dihydroxy-9-oxo-16-allenyl-20-methyl-13-trans prostenoic acid | dl-9α,11α-trihydroxy-16-allenyl-20-methyl-13-trans prostenoic acid |
| 52 | dl-11α,16-dihydroxy-9-oxo-16-allenyl-20-ethyl-13-trans prostenoic aicd | dl-9α,11α,16-trihydroxy-16-allenyl-20-ethyl-13-trans prostenoic acid |
| 53 | dl-11α,16-dihydroxy-9-oxo-16-allenyl-20-nor-2-homo-13-trans prostenoic acid | dl-9α,11α,16-trihydroxy-16-allenyl-20-nor-2-homo-13-trans prostenoic acid |
| 54 | dl-11α,16-dihydroxy-9-oxo-16-allenyl-2-homo-13-trans prostenoic acid | dl-9α,11α,16-trihydroxy-16-allenyl-2-homo-13-trans prostenoic acid |
| 55 | dl-11α,16-dihydroxy-9-oxo-16-allenyl-20-methyl-2-homo-13-trans prostenoic acid | dl-9α,11α,16-trihydroxy-16-allenyl-20-methyl-2-homo-13-trans prostenoic acid |
| 56 | dl-11α,16-dihydroxy-9-oxo-16-allenyl-20-ethyl-2-homo-13-trans prostenoic acid | dl-9α,11α,16-trihydroxy-16-allenyl-20-ethyl-2-homo-13-trans prostenoic acid |
| 57 | dl-11α,16-dihydroxy-9-oxo-16-allenyl-20-nor-3-thia-13-trans prostenoic acid | dl-9α,11α,16-trihydroxy-16-allenyl-20-nor-3-thia-13-trans prostenoic acid |
| 58 | dl-11α,16-dihydroxy-9-oxo-16-allenyl-3-thia-13-trans prostenoic acid | dl-9α,11α,16-trihydroxy-16-allenyl-3-thia-13-trans prostenoic acid |
| 59 | dl-11α,16-dihydroxy-9-oxo-16-allenyl-20-methyl-3-thia-13-trans prostenoic acid | dl-9α,11α,16-trihydroxy-16-allenyl-20-methyl-3-thia-13-trans prostenoic acid |
| 60 | dl-11α,16-dihydroxy-9-oxo-16-allenyl-20-ethyl-3-thia-13-trans prostenoic acid | dl-9α,11α,16-trihydroxy-16-allenyl-20-ethyl-3-thia-13-trans prostenoic acid |
| 61 | dl-11α,16-dihydroxy-9-oxo-16-allenyl-20-nor-3-oxa-13-trans prostenoic acid | dl-9α,11α,16-trihydroxy-16-allenyl-20-nor-3-oxa-13-trans prostenoic acid |
| 62 | dl-11α,16-dihydroxy-9-oxo-16-allenyl-3-oxa-13-trans prostenoic acid | dl-9α,11α,16-trihydroxy-16-allenyl-3-oxa-13-trans prostenoic acid |
| 63 | dl-11α,16-dihydroxy-9-oxo-16-allenyl-20-methyl-3-oxa-13-trans prostenoic acid | dl-9α,11α,16-trihydroxy-16-allenyl-20-methyl-3-oxa-13-trans prostenoic acid |
| 64 | dl-11α,16-dihydroxy-9-oxo-16-allenyl-20-ethyl-3-oxa-13-trans prostenoic acid | dl-9α,11α,16-trihydroxy-16-allenyl-20-ethyl-3-oxa-13-trans prostenoic acid |
| 65 | nat-11α,16-dihydroxy-9-oxo-16-allenyl-20-nor-13-trans prostenoic acid | nat-9α,11α,16-trihydroxy-16-allenyl-20-nor-13-trans prostenoic acid |
| 66 | nat-11α,16-dihydroxy-9-oxo-16-allenyl-13-trans prostenoic acid | nat-9α,11α,16-trihydroxy-16-allenyl-13-trans prostenoic acid |
| 67 | nat-11α,16-dihydroxy-9-oxo-16-allenyl-20-methyl-13-trans prostenoic acid | nat-9α,11α,16-trihydroxy-16-allenyl-20-methyl-13-trans prostenoic acid |
| 68 | nat-11α,16-dihydroxy-9-oxo-16-allenyl-20-ethyl-13-trans prostenoic acid | nat-9α,11α,16-trihydroxy-16-allenyl-20-ethyl-13-trans prostenoic acid |

| EXAMPLE | STARTING PROSTAGLANDIN OF THE PGE SERIES | PRODUCT PROSTAGLANDIN OF THE 11-DEOXY PGF1α SERIES |
|---|---|---|
| 69 | dl-16-hydroxy-9-oxo-16-allenyl-20-nor-2-nor-13-trans prostenoic acid | dl-9α,16-dihydroxy-16-allenyl-20-nor-2-nor-13-trans prostenoic acid |
| 70 | dl-16-hydroxy-9-oxo-16-allenyl-2-nor-13-trans prostenoic acid | dl-9α,16-dihydroxy-16-allenyl-2-nor-13-trans prostenoic acid |
| 71 | dl-16-hydroxy-9-oxo-16-allenyl-20-methyl-2-nor-13-trans prostenoic acid | dl-9α,16-dihydroxy-16-allenyl-20-methyl-2-nor-13-trans prostenoic acid |
| 72 | dl-16-hydroxy-9-oxo-16-allenyl-20-ethyl-2-nor-13-trans prostenoic acid | dl-9α,16-dihydroxy-16-allenyl-20-ethyl-2-nor-13-trans prostenoic acid |
| 73 | dl-16-hydroxy-9-oxo-16-allenyl-20-nor-13-trans prostenoic acid | dl-9α,16-dihydroxy-16-allenyl-20-nor-13-trans prostenoic acid |
| 74 | dl-16-hydroxy-9-oxo-16-allenyl-13-trans prostenoic aicd | dl-9α,16-dihydroxy-16-allenyl-13-trans prostenoic acid |
| 75 | dl-16-hydroxy-9-oxo-16-allenyl-20-methyl-13-trans prostenoic acid | dl-9α,16-dihydroxy-16-allenyl-20-methyl-13-trans prostenoic acid |
| 76 | dl-16-hydroxy-9-oxo-16-allenyl-20-ethyl-13-trans prostenoic acid | dl-9α,16-dihydroxy-16-allenyl-20-ethyl-13-trans prostenoic acid |
| 77 | dl-16-hydroxy-9-oxo-16-allenyl-20-nor-2-homo-13-trans prostenoic acid | dl-9α,16-dihydroxy-16-allenyl-20-nor-2-homo-13-trans prostenoic acid |
| 78 | dl-16-hydroxy-9-oxo-16-allenyl-2-homo-13-trans prostenoic acid | dl-9α,16-dihydroxy-16-allenyl-2-homo-13-trans prostenoic acid |
| 79 | dl-16-hydroxy-9-oxo-16-allenyl-20-methyl-2-homo-13-trans prostenoic acid | dl-9α,16-dihydroxy-16-allenyl-20-methyl-2-homo-13-trans prostenoic acid |
| 80 | dl-16-hydroxy-9-oxo-16-allenyl-20-ethyl-2-homo-13-trans prostenoic acid | dl-9α,16-dihydroxy-16-allenyl-20-ethyl-2-homo-13-trans prostenoic acid |
| 81 | dl-16-hydroxy-9-oxo-16-allenyl-20-nor-3-thia-13-trans prostenoic acid | dl-9α,16-dihydroxy-16-allenyl-20-nor-3-thia-13-trans prostenoic acid |
| 82 | dl-16-hydroxy-9-oxo-16-allenyl-3-thia-13-trans prostenoic acid | dl-9α,16-dihydroxy-16-allenyl-3-thia-13-trans prostenoic acid |

| EXAMPLE | STARTING PROSTAGLANDIN OF THE PGE SERIES | PRODUCT PROSTAGLANDIN THE 11-DEOXY PGF1β SERIES |
|---|---|---|
| 83 | dl-16-hydroxy-9-oxo-16-allenyl-20-methyl-3-thia-13-trans prostenoic acid | dl-9α,16-dihydroxy-16-allenyl-20-methyl-3-thia-13-trans prostenoic acid |

| EXAMPLE | STARTING PROSTAGLANDIN OF THE PGE SERIES | PRODUCT PROSTAGLANDIN OF THE 11-DEOXY PGF1α SERIES |
|---|---|---|
| 84 | dl-16-hydroxy-9-oxo-16-allenyl-20-ethyl-3-thia-13-trans prostenoic acid | dl-9α,16-dihydroxy-16-allenyl-20-ethyl-3-thia-13-trans prostenoic acid |
| 85 | dl-16-hydroxy-9-oxo-16-allenyl-20-nor-3-oxa-13-trans prostenoic acid | dl-9α,16-dihydroxy-16-allenyl-20-nor-3-oxa-13-trans prostenoic acid |
| 86 | dl-16-hydroxy-9-oxo-16-allenyl-3-oxa-13-trans prostenoic acid | dl-9α,16-dihydroxy-16-allenyl-3-oxa-13-trans prostenoic acid |
| 87 | dl-16-hydroxy-9-oxo-16-allenyl-20-methyl-3-oxa-13-trans prostenoic acid | dl-9α,16-dihydroxy-16-allenyl-20-methyl-3-oxa-13-trans prostenoic acid |
| 88 | dl-16-hydroxy-9-oxo-16-allenyl-20-ethyl-3-oxa-13-trans prostenoic acid | dl-9α,16-dihydroxy-16-allenyl-20-ethyl-3-oxa-13-trans prostenoic acid |

TABLE I (Continued)

Treatment of the PGE1 derivatives of Examples of Table I with sodium borohydride by the procedure of Reference Example 8 is productive of the PGFα and PGFβ derivatives of Examples 89 to 132 of Table I. Although the 9β product is listed it will be understood that the corresponding 9α is also produced by the exemplified reaction. The 9α and 9β products are separable however, by silica gel chromatography.

| EXAMPLE | STARTING PROSTAGLANDIN OF THE PGE SERIES | PRODUCT PROSTAGLANDIN OF THE PGF1β SERIES |
|---|---|---|
| 89 | dl-11α,16-dihydroxy-9-oxo-16-allenyl-20-nor-2-nor-13-trans prostenoic acid | dl-9β,11α,16-trihydroxy-16-allenyl-20-nor-2-nor-13-trans prostenoic acid |
| 90 | dl-11α,16-dihydroxy-9-oxo-16-allenyl-2-nor-13-trans prostenoic acid | dl-9β,11α,16-trihydroxy-16-allenyl-2-nor-13-trans prostenoic acid |
| 91 | dl-11α,16-dihydroxy-9-oxo-16-allenyl-20-methyl-2-nor-13-trans prostenoic acid | dl-9β,11α,16-trihydroxy-16-allenyl-20-methyl-2-nor-13-trans prostenoic acid |
| 92 | dl-11α,16-dihydroxy-9-oxo-16-allenyl-20-ethyl-2-nor-13-trans prostenoic acid | dl-9β,11α,16-trihydroxy-16-allenyl-20-ethyl-2-nor-13-trans prostenoic acid |
| 93 | dl-11α,16-dihydroxy-9-oxo-16-allenyl-20-nor-13-trans prostenoic acid | dl-9β,11α,16-trihydroxy-16-allenyl-20-nor-13-trans prostenoic acid |
| 94 | dl-11α,16-dihydroxy-9-oxo-16-allenyl-13-trans prostenoic acid | dl-9β,11α,16-trihydroxy-16-allenyl-13-trans prostenoic acid |
| 95 | dl-11α,16-dihydroxy-9-oxo-16-allenyl-20-methyl-13-trans prostenoic acid | dl-9β,11α,16-trihydroxy-16-allenyl-20-methyl-13-trans prostenoic acid |
| 96 | dl-11α,16-dihydroxy-9-oxo-16-allenyl-20-ethyl-13-trans prostenoic acid | dl-9β,11α,16-trihydroxy-16-allenyl-20-ethyl-13-trans prostenoic acid |
| 97 | dl-11α,16-dihydroxy-9-oxo-16-allenyl-20-nor-2-homo-13-trans prostenoic acid | dl-9β,11α,16-trihydroxy-16-allenyl-20-nor-2-homo-13-trans prostenoic acid |
| 98 | dl-11α,16-dihydroxy-9-oxo-16-allenyl-2-homo-13-trans prostenoic acid | dl-9β,11α,16-trihydroxy-16-allenyl-2-homo-13-trans prostenoic acid |
| 99 | dl-11α,16-dihydroxy-9-oxo-16-allenyl-20-methyl-2-homo-13-trans prostenoic acid | dl-9β,11α,16-trihydroxy-16-allenyl-20-methyl-2-homo-13-trans prostenoic acid |
| 100 | dl-11α,16-dihydroxy-9-oxo-16-allenyl-20-ethyl-2-homo-13-trans prostenoic acid | dl-9β,11α,16-trihydroxy-16-allenyl-20-ethyl-2-homo-13-trans prostenoic acid |
| 101 | dl-11α,16-dihydroxy-9-oxo-16-allenyl-20-nor-3-thia-13-trans prostenoic acid | dl-9β,11α,16-trihydroxy-16-allenyl-20-nor-3-thia-13-trans prostenoic acid |
| 102 | dl-11α,16-dihydroxy-9-oxo-16-allenyl-3-thia-13-trans prostenoic acid | dl-9β,11α,16-trihydroxy-16-allenyl-3-thia-13-trans prostenoic acid |
| 103 | dl-11α,16-dihydroxy-9-oxo-16-allenyl-20-methyl-3-thia-13-trans prostenoic acid | dl-9β,11α,16-trihydroxy-16-allenyl-20-methyl-3-thia-13-trans prostenoic acid |
| 104 | dl-11α,16-dihydroxy-9-oxo-16-allenyl-20-ethyl-3-thia-13-trans prostenoic acid | dl-9β,11α,16-trihydroxy-16-allenyl-20-ethyl-3-thia-13-trans prostenoic acid |
| 105 | dl-11α,16-dihydroxy-9-oxo-16-allenyl-20-nor-3-oxa-13-trans prostenoic acid | dl-9β,11α,16-trihydroxy-16-allenyl-20-nor-3-oxa-13-trans prostenoic acid |
| 106 | dl-11α,16-dihydroxy-9-oxo-16-allenyl-3-oxa-13-trans prostenoic acid | dl-9β,11α,16-trihydroxy-16-allenyl-3-oxa-13-trans prostenoic acid |
| 107 | dl-11α,16-dihydroxy-9-oxo-16-allenyl-20-methyl-3-oxa-13-trans prostenoic acid | dl-9β,11α,16-trihydroxy-16-allenyl-20-methyl-3-oxa-13-trans prostenoic acid |
| 108 | dl-11α,16-dihydroxy-9-oxo-16-allenyl-20-ethyl-3-oxa-13-trans prostenoic acid | dl-9β,11α,16-trihydroxy-16-allenyl-20-ethyl-3-oxa-13-trans prostenoic acid |
| 109 | nat-11α,16-dihydroxy-9-oxo-16-allenyl-20-nor-13-trans prostenoic acid | nat-9β,11α,16-trihydroxy-16-allenyl-20-nor-13-trans prostenoic acid |
| 110 | nat-11α,16-dihydroxy-9-oxo-16-allenyl-13-trans prostenoic acid | nat-9β,11α,16-trihydroxy-16-allenyl-13-trans prostenoic acid |
| 111 | nat-11α,16-dihydroxy-9-oxo-16-allenyl-20-methyl-13-trans prostenoic acid | nat-9β,11α,16-trihydroxy-16-allenyl-20-methyl-13-trans prostenoic acid |
| 112 | nat-11α,16-dihydroxy-9-oxo-16-allenyl-20-ethyl-13-trans prostenoic acid | nat-9β,11α,16-trihydroxy-16-allenyl-20-ethyl-13-trans prostenoic acid |

| EXAMPLE | STARTING PROSTAGLANDIN OF THE PGE SERIES | PRODUCT PROSTAGLANDIN OF THE 11-DEOXY PGF1β SERIES |
|---|---|---|
| 113 | dl-16-hydroxy-9-oxo-16-allenyl-20-nor-2-nor-13-trans prostenoic acid | dl-9β,16-dihydroxy-16-allenyl-20-nor-2-nor-13-trans prostenoic acid |

-continued

| | | |
|---|---|---|
| 114 | dl-16-hydroxy-9-oxo-16-allenyl-2-nor-13-trans prostenoic acid | dl-9β,16-dihydroxy-16-allenyl-2-nor-13-trans prostenoic acid |
| 115 | dl-16-hydroxy-9-oxo-16-allenyl-20-methyl-2-nor-13-trans prostenoic acid | dl-9β,16-dihydroxy-16-allenyl-20-methyl-2-nor-13-trans prostenoic acid |
| 116 | dl-16-hydroxy-9-oxo-16-allenyl-20-ethyl-2-nor-13-trans prostenoic acid | dl-9β,16-dihydroxy-16-allenyl-20-ethyl-2-nor-13-trans prostenoic acid |
| 117 | dl-16-hydroxy-9-oxo-16-allenyl-20-nor-13-trans prostenoic acid | dl-9β,16-dihydroxy-16-allenyl-20-nor-13-trans prostenoic acid |
| 118 | dl-16-hydroxy-9-oxo-16-allenyl-13-trans prostenoic acid | dl-9β,16-dihydroxy-16-allenyl-13-trans prostenoic acid |
| 119 | dl-16-hydroxy-9-oxo-16-allenyl-20-methyl-13-trans prostenoic acid | dl-9β,16-dihydroxy-16-allenyl-20-methyl-13-trans prostenoic acid |
| 120 | dl-16-hydroxy-9-oxo-16-allenyl-20-ethyl-13-trans prostenoic acid | dl-9β,16-dihydroxy-16-allenyl-20-ethyl-13-trans prostenoic acid |
| 121 | dl-16-hydroxy-9-oxo-16-allenyl-20-nor-2-homo-13-trans prostenoic acid | dl-9β,16-dihydroxy-16-allenyl-20-nor-2-homo-13-trans prostenoic acid |
| 122 | dl-16-hydroxy-9-oxo-16-allenyl-2-homo-13-trans prostenoic acid | dl-9β,16-dihydroxy-16-allenyl-2-homo-13-trans prostenoic acid |
| 123 | dl-16-hydroxy-9-oxo-16-allenyl-20-methyl-2-homo-13-trans prostenoic acid | dl-9β,16-dihydroxy-16-allenyl-20-methyl-2-homo-13-trans prostenoic acid |
| 124 | dl-16-hydroxy-9-oxo-16-allenyl-20-ethyl-2-homo-13-trans prostenoic acid | dl-9β,16-dihydroxy-16-allenyl-20-ethyl-2-homo-13-trans prostenoic acid |
| 125 | dl-16-hydroxy-9-oxo-16-allenyl-20-nor-3-thia-13-trans prostenoic acid | dl-9β,16-dihydroxy-16-allenyl-20-nor-3-thia-13-trans prostenoic acid |
| 126 | dl-16-hydroxy-9-oxo-16-allenyl-3-thia-13-trans prostenoic acid | dl-9β,16-dihydroxy-16-allenyl-3-thia-13-trans prostenoic acid |
| 127 | dl-16-hydroxy-9-oxo-16-allenyl-20-methyl-3-thia-13-trans prostenoic acid | dl-9β,16-dihydroxy-16-allenyl-20-methyl-3-thia-13-trans prostenoic acid |
| 128 | dl-16-hydroxy-9-oxo-16-allenyl-20-ethyl-3-thia-13-trans prostenoic acid | dl-9β,16-dihydroxy-16-allenyl-20-ethyl-3-thia-13-trans prostenoic acid |
| 129 | dl-16-hydroxy-9-oxo-16-allenyl-20-nor-3-oxa-13-trans prostenoic acid | dl-9β,16-dihydroxy-16-allenyl-20-nor-3-oxa-13-trans prostenoic acid |
| 130 | dl-16-hydroxy-9-oxo-16-allenyl-3-oxa-13-trans prostenoic acid | dl-9β,16-dihydroxy-16-allenyl-3-oxa-13-trans prostenoic acid |
| 131 | dl-16-hydroxy-9-oxo-16-allenyl-20-methyl-3-oxa-13-trans prostenoic acid | dl-9β,16-dihydroxy-16-allenyl-20-methyl-3-oxa-13-trans prostenoic acid |
| 132 | dl-16-hydroxy-9-oxo-16-allenyl-20-ethyl-3-oxa-13-trans prostenoic acid | dl-9β,16-dihydroxy-16-allenyl-20-ethyl-3-oxa-13-trans prostenoic acid |

TABLE II

Treatment of the appropriate cyclopentenones of Table B with the lithiocuprates derived from the vinylstannanes or vinyliodides of Reference Examples 4 and 6 by the procedure of Reference Examples 5 is productive of the PGE₂ derivatives of Examples 1–28 of Table II.

| EXAMPLE | VINYL IODIDE | CYCLOPENTONE | PRODUCT PROSTAGLANDIN OF THE PGE₂ SERIES |
|---|---|---|---|
| 1 | 1-trans-iodo-4-allenyl-4-trimethylsiloxy-1-heptene | 2-(5-carbotrimethylsiloxypent-2-cis-enyl)-4-trimethylsiloxycyclopent-2-en-1-one | dl-11α,16-dihydroxy-9-oxo-16-allenyl-20-nor-2-nor-5-cis-13-trans prostadienoic acid |
| 2 | 1-trans-iodo-4-allenyl-4-trimethylsiloxy-1-octene | 2-(5-carbotrimethylsiloxypent-2-cis-enyl)-4-trimethylsiloxycyclopent-2-en-1-one | dl-11α,16-dihydroxy-9-oxo-16-allenyl-2-nor-5-cis-13-trans prostadienoic acid |
| 3 | 1-trans-iodo-4-allenyl-4-trimethylsiloxy-1-nonene | 2-(5-carbotrimethylsiloxypent-2-cis-enyl)-4-trimethylsiloxycyclopent-2-en-1-one | dl-11α,16-dihydroxy-9-oxo-16-allenyl-20-methyl-2-nor-5-cis-13-trans prostadienoic acid |
| 4 | 1-trans-iodo-4-allenyl-4-trimethylsiloxy-1-decene | 2-(5-carbotrimethylsiloxypent-2-cis-enyl)-4-trimethylsiloxycyclopent-2-en-1-one | dl-11α,16-dihydroxy-9-oxo-16-allenyl-20-ethyl-2-nor-5-cis-13-trans prostadienoic acid |
| 5 | 1-trans-iodo-4-allenyl-4-trimethylsiloxy-1-heptene- | 2-(6-carbotrimethylsiloxyhex-2-cis-enyl)-4-trimethylsiloxycyclopent-2-en-1-one | dl-11α,16-dihydroxy-9-oxo-16-allenyl-20-nor-5-cis-13-trans prostadienoic acid |
| 6 | 1-trans-iodo-4-allenyl-4-trimethylsiloxy-1-octene | 2-(6-carbotrimethylsiloxyhex-2-cis-enyl)-4-trimethylsiloxycyclopent-2-en-1-one | dl-11α,16-dihydroxy-9-oxo-16-allenyl-5-cis-13-trans prostadienoic acid |
| 7 | 1-trans-iodo-4-allenyl-4-trimethylsiloxy-1-nonene | 2-(6-carbotrimethylsiloxyhex-2-cis-enyl)-4-trimethylsiloxycyclopent-2-en-1-one | dl-11α,16-dihydroxy-9-oxo-16-allenyl-20-methyl-5-cis-13-trans prostadienoic acid |
| 8 | 1-trans-iodo-4-allenyl-4-trimethylsiloxy-1-decene | 2-(6-carbotrimethylsiloxyhex-2-cis-enyl)-4-trimethylsiloxycyclopent-2-en-1-one | dl-11α,16-dihydroxy-9-oxo-16-allenyl-20-ethyl-5-cis-13-trans prostadienoic acid |
| 9 | 1-trans-iodo-4-allenyl-4-trimethylsiloxy-1-heptene | 2-(7-carbotrimethylsiloxyhept-2-cis-enyl)-4-trimethylsiloxycyclopent-2-en-1-one | dl-11α,16-dihydroxy-9-oxo-16-allenyl-20-nor-2-homo-5-cis-13-trans prostadienoic acid |
| 10 | 1-trans-iodo-4-allenyl-4-trimethylsiloxy-1-octene | 2-(7-carbotrimethylsiloxyhept-2-cis-enyl)-4-trimethylsiloxycyclopent-2-en-1-one | dl-11α,16-dihydroxy-9-oxo-16-allenyl-2-homo-5-cis-13-trans prostadienoic acid |
| 11 | 1-trans-iodo-4-allenyl-4-trimethylsiloxy-1-nonene | 2-(7-carbotrimethylsiloxyhept-2-cis-enyl)-4-trimethylsiloxycyclopent-2-en-1-one | dl-11α,16-dihydroxy-9-oxo-16-allenyl-20-methyl-2-homo-5-cis-13-trans prostadienoic acid |
| 15 | 1-trans-iodo-4-allenyl-4-trimethylsiloxy-1-nonene | 2-(6-carbotrimethylsiloxyhex-2-cis-enyl)-4R-trimethylsiloxycyclopent-2-en-1-one | nat-11α,16-dihydroxy-9-oxo-16-allenyl-20-methyl-5-cis-13-trans prostadienoic acid |
| 16 | 1-trans-iodo-4-allenyl-4-trimethylsiloxy-1-decene | 2-(6-carbotrimethylsiloxyhex-2-cis-enyl)-4R-trimethylsiloxycyclopent-2-en-1-one | nat-11α,16-dihydroxy-9-oxo-16-allenyl-20-ethyl-5-cis-13-trans prostadienoic acid |

| EXAMPLE | VINYL IODIDE | CYCLOPENTENONE | PRODUCT PROSTAGLANDIN OF THE 11-DEOXY PGE₂ SERIES |
|---|---|---|---|
| 17 | 1-trans-iodo-4-allenyl-4-trimethylsiloxy-1-heptene | 2-(5-carboethoxypent-2-cis-enyl) cyclopent-2-en-1-one | dl-16-hydroxy-9-oxo-16-allenyl-20-nor-2-nor-5-cis-13-trans prostadienoic acid |
| 18 | 1-trans-iodo-4-allenyl-4-trimethylsiloxy-1-octene | 2-(5-carboethoxypent-2-cis-enyl) cyclopent-2-en-1-one | dl-16-hydroxy-9-oxo-16-allenyl-2-nor-5-cis-13-trans prostadienoic acid |

-continued

| | | | |
|---|---|---|---|
| 19 | -trans-iodo-4-allenyl-4-trimethylsiloxy-1-nonene | 2-(5-carboethoxypent-2-cis-enyl)cyclopent-2-en-1-one | dl-16-hydroxy-9-oxo-16-allenyl-2-methyl-2-nor-5-cis-13-trans prostadienoic acid |
| 20 | -trans-iodo-4-allenyl-4-trimethylsiloxy-1-decene | 2-(5-carboethoxypent-2-cis-enyl)cyclopent-2-en-1-one | dl-16-hydroxy-9-oxo-16-allenyl-20-ethyl-2-nor-5-cis-13-trans prostadienoic acid |
| 21 | -trans-iodo-4-allenyl-4-trimethylsiloxy-1-heptene | 2-(6-carboethoxyhex-2-cis-enyl)cyclopent-2-en-1-one | dl-16-hydroxy-9-oxo-16-allenyl-20-nor-5-cis-13-trans prostadienoic acid |
| 22 | -trans-iodo-4-allenyl-4-trimethylsiloxy-1-octene | 2-(6-carboethoxyhex-2-cis-eneyl)cyclopent-2-en-1-one | dl-16-hydroxy-9-oxo-16-allenyl-5-cis-13-trans prostadienoic acid |
| 23 | -trans-iodo-4-allenyl-4-trimethylsiloxy-1-nonene | 2-(6-carboethoxyhex-2-cis-enyl)cyclopent-2-en-1-one | dl-16-hydroxy-9-oxo-16-allenyl-20-methyl-5-cis-13-trans prostadienoic acid |
| 24 | -trans-iodo-4-allenyl-4-trimethylsiloxy-1-decene | 2-(6-carboethoxyhex-2-cis-enyl)cyclopent-2-en-1-one | dl-16-hydroxy-9-oxo-16-allenyl-20-ethyl-5-cis-13-trans prostadienoic acid |
| 25 | -trans-iodo-4-allenyl-4-trimethylsiloxy-1-heptene | 2-(7-carboethoxyhept-2-cis-enyl)cyclopent-2-en-1-one | dl-16-hydroxy-9-oxo-16-allenyl-20-nor-2-homo-5-cis-13-trans prostadienoic acid |
| 26 | -trans-iodo-4-allenyl-4-trimethylsiloxy-1-octene | 2-(7-carboethoxyhept-2-cis-enyl)cyclopent-2-en-1-one | dl-16-hydroxy-9-oxo-16-allenyl-2-homo-5-cis-13-trans prostadienoic acid |
| 27 | -trans-iodo-4-allenyl-4-trimethylsiloxy-1-nonene | 2-(7-carboethoxyhept-2-cis-enyl)cyclopent-2-en-1-one | dl-16-hydroxy-9-oxo-16-allenyl-20-methyl-2-homo-5-cis-13-trans prostadienoic acid |
| 28 | -trans-iodo-4-allenyl-4-trimethylsiloxy-1-decene | 2-(7-carboethoxyhept-2-cis-enyl)cyclopent-2-en-1-one | dl-16-hydroxy-9-oxo-16-allenyl-20-ethyl-2-homo-5-cis-13-trans prostadienoic acid |

TABLE II (Continued)

Treatment of the PGE$_2$ derivatives of Examples of Table II with lithium perhydro-9β-boraphenalyl hydride by the procedure of Reference Example 7 is productive of the PGF$_{2α}$ derivatives of Examples of Table II.

| EXAMPLE | STARTING PROSTAGLANDIN OF THE PGE SERIES | PRODUCT PROSTAGLANDIN OF THE PGF$_{2α}$ SERIES |
|---|---|---|
| 29 | dl-11α,16-dihydroxy-9-oxo-16-allenyl-20-nor-2-nor-5-cis-13-trans prostadienoic acid | dl-9α,11α-trihydroxy-16-allenyl-2-nor-2-nor-5-cis-13-trans prostadienoic acid |
| 30 | dl-11α,16-dihydroxy-9-oxo-16-allenyl-2-nor-5-cis-13-trans prostadienoic acid | dl-9α,11α,16-trihydroxy-16-allenyl-2-nor-5-cis-13-trans prostadienic acid |
| 31 | dl-11α,16-dihydroxy-9-oxo-16-allenyl-20-methyl-2-nor-5-cis-13-trans prostadienoic acid | dl-9α,11α,16-trihydroxy-16-allenyl-20-methyl-2-nor-5-cis-13-trans prostadienoic acid |
| 32 | dl-11α,16-dihydroxy-9-oxo-16-allenyl-20-ethyl-2-nor-5-cis-13-trans prostadienoic acid | di-9α,11α,16-trihydroxy-16-allenyl-20-ethyl-2-nor-5-cis-13-trans prostadienoic acid |
| 33 | dl-11,16-dihydroxy-9-oxo-16-allenyl-20-nor-5-cis-13-trans prostadienoic acid | dl-9,11,16-trihyroxy-16-allenyl-20-nor-5-cis-13-trans prostadienoic acid |
| 34 | dl-11,16-dihydroxy-9-oxo-16-allenyl-5-cis-13-trans prostadienoic acid | dl-9α,11α,16-trihydroxy-16-allenyl-5-cis-13-trans prostadienoic acid |
| 35 | dl-11α,16-dihydroxy-9-oxo-16-allenyl-20-methyl-5-cis-13-trans prostadienoic acid | dl-9α,11α,16-trihydroxy-16-allenyl-20-methyl-5-cis-13-trans prostadienoic acid |
| 36 | dl-11α,16-dihydroxy-9-oxo-16-allenyl-20-ethyl-5-cis-13-trans prostadienoic acid | dl-9α,11α,16-trihydroxy-16-allenyl-20-ethyl-5-cis-13-trans prostadienoic acid |
| 37 | dl-11α,16-dihydroxy-9-oxo-16-allenyl-20-nor-2-homo-5-cis-13-trans prostadenoic acid | dl-9α,11α,16-trihydroxy-16-allenyl-20-nor-2-homo-5-cis-13-trans prostadienoic acid |
| 38 | dl-11α,16-dihydroxy-9-oxo-16-allenyl-2-homo-5-cis-13-trans prostadienoic acid | dl-9-α,11α,16-trihydroxy-16-allenyl-2-homo-5-cis-13-trans prostadienoic acid |
| 39 | dl-11α,16-dihydroxy-9-oxo-16-allenyl-20-methyl-2-homo-5-cis-13-trans prostadienoic acid | dl-9α,11α,16-trihydroxy-16-allenyl-20-methyl-2-homo-5-cis-13-trans prostadienoic acid |
| 40 | dl-11α,16-dihydroxy-9-oxo-16-allenyl-20-ethyl-2-homo-5-cis-13-trans prostadienoic acid | dl-9α,11α,16-trihydroxy-16-allenyl-20-ethyl-2-homo-5-cis-13-trans prostadienoic acid |
| 41 | nat-11α,16-dihydroxy-9-oxo-16-allenyl-20-nor-5-cis-13-trans prostadienoic acid | nat-9α,11α16-trihydroxy-16-allenyl-20-nor-5-cis-13-trans prostadienoic acid |
| 42 | nat-11α,16-dihydroxy-9-oxo-16-allenyl-5-cis-13-trans prostadienoic acid | nat-9α,11α,16-trihydroxy-16-allenyl-5-cis-13-trans prostadienoic acid |
| 43 | nat-11α,16-dihydroxy-9-oxo-16-allenyl-20-methyl-5-cis-13-trans prostadienoic acid | nat-9α,11α,16-trihydroxy-16-allenyl-20-methyl-5-cis-13-trans prostadienoic acid |
| 44 | nat-11α,16-dihydroxy-9-oxo-16-allenyl-20-ethyl-5-cis-13-trans prostadienoic acid | nat-9α,11α,16-trihydroxy-16-allenyl-20-ethyl-5-cis-13-trans prostadienoic acid |

| EXAMPLE | STARTING PROSTAGLANDIN OF THE PGE SERIES | PRODUCT PROSTAGLANDIN OF THE 11-DEOXY PGF$_{2α}$ SERIES |
|---|---|---|
| 45 | dl-16-hydroxy-9-oxo-16-allenyl-20-nor-2-nor-5-cis-13-trans prostadienoic acid | dl-9α,16-dihydroxy-16-allenyl-20-nor-2-nor-5-cis-13-trans prostadienoic acid |
| 46 | dl-16-hydroxy-9-oxo-16-allenyl-2-nor-5-cis-13-trans prostadienoic acid | dl-9α,16-dihydroxy-16-allenyl-2-nor-5-cis-13-trans prostadienoic acid |
| 47 | dl-16-hydroxy-9-oxo-16-allenyl-20-methyl-2-nor-5-cis-13-trans prostadienoic acid | dl-9α,16-dihydroxy-16-allenyl-20-methyl-2-nor-5-cis-13-trans prostadienoic acid |
| 48 | dl-16-hydroxy-9-oxo-16-allenyl-20-ethyl-2-nor-5-cis-13-trans prostadienoic acid | dl-9α,16-dihydroxy-16-allenyl-20-ethyl-2-nor-5-cis-13-trans prostadienoic acid |
| 49 | dl-16-hydroxy-9-oxo-16-allenyl-20-nor-5-cis-13-trans prostadienoic acid | dl-9α,16-dihydroxy-16-allenyl-20-nor-5-cis-13-trans prostadienoic acid |
| 50 | dl-16-hydroxy-9-oxo-16-alleny-5-cis-13-trans prostadienoic acid | dl-9α,16-dihydroxy-16-allenyl-5-cis-13-trans prostadienoic acid |
| 51 | dl-16-hydroxy-9-oxo-16-allenyl-20-methyl-5-cis-13-trans prostadienoic acid | dl-9α,16-dihydroxy-16-allenyl-20-methyl-5-cis-trans prostadienoic acid |
| 52 | dl-16-hydroxy-9-oxo-16-allenyl-20-ethyl-5-cis-13-trans prostadienoic acid | dl-9α,16-dihydroxy-16-allenyl-20-ethyl-5-cis-13-trans prostadienoic acid |

| | -continued | |
|---|---|---|
| 53 | dl-16-hydroxy-9-oxo-16-allenyl-20-nor-2-homo-5-cis-13-trans prostadienoic acid | dl-9α,16-dihydroxy-16-allenyl-20-nor-2-homo-5-cis-13-trans prostadienoic acid |
| 54 | dl-16-hydroxy-9-oxo-16-allenyl-2-homo-5-cis-13-trans prostadienoic acid | dl-9α,16-dihydroxy-16-allenyl-2-homo-5-cis-13-trans prostadienoic acid |
| 55 | dl-16-hydroxy-9-oxo-16-allenyl-20-methyl-2-homo-5-cis-13-trans prostadienoic acid | dl-9α,16-dihydroxy-16-allenyl-20-methyl-2-homo-5-cis-13-trans prostadienoic acid |
| 56 | dl-16-hydroxy-9-oxo-16-allenyl-20-ethyl-2-homo-5-cis-13-trans prostadienoic acid | dl-9α,16-dihydroxy-16-allenyl-20-ethyl-2-homo-5-cis-13-trans prostadienoic acid |

TABLE II (Continued)

Treatment of the PGE$_2$ derivatives of Examples of Table II with sodium borohydride by the procedure of Reference Example 8 is productive of the PGFα and PGFβ derivatives of Examples 57 to 84 of Table II.

Although the 9β product is listed in the table which follows, it will be understood that the corresponding 9α-hydroxy product to the listed 9β-product is also produced by the exemplified reaction. However, the 9α and 9β-hydroxy is separable by silica gel chromatography.

| EXAMPLE | STARTING PROSTAGLANDIN OF THE PGE SERIES | PRODUCT PROSTAGLANDIN OF THE PGF$_{2\beta}$ SERIES |
|---|---|---|
| 57 | dl-11α,16-dihydroxy-9-oxo-16-allenyl-20-nor-2-nor-5-cis-13-trans prostadienoic acid | dl-9β,11α,16-trihydroxy-16-allenyl-20-nor-2-nor-5-cis-13-trans prostadienoic acid |
| 58 | dl-11α,16-dihydroxy-9-oxo-16-allenyl-2-nor-5-cis-13-trans prostadienoic acid | dl-9β,11α,16-trihydroxy-16-allenyl-2-nor-5-cis-13-trans prostadienoic acid |
| 59 | dl-11α,16-dihydroxy-9-oxo-16-allenyl-20-methyl-2-nor-5-cis-13-trans prostadienoic acid | dl-9β,11α,16-trihydroxy-16-allenyl-20-methyl-2-nor-5-cis-13-trans prostadienoic acid |
| 60 | dl-11α,16-dihydroxy-9-oxo-16-allenyl-20-ethyl-2-nor-5-cis-13-trans prostadienoic acid | dl-9β,11α,16-trihydroxy-16-allenyl-20-ethyl-2-nor-5-cis-13-trans prostadienoic acid |
| 61 | dl-11α,16-dihydroxy-9-oxo-16-allenyl-20-nor-5-cis-13-trans prostadienoic acid | dl-9β,11α,16-trihydroxy-16-allenyl-20-nor-5-cis-13-trans prostadienoic acid |
| 62 | dl-11α,16-dihydroxy-9-oxo-16-allenyl-5-cis-13-trans prostadienoic acid | dl-9β,11α,16-trihydroxy-16-allenyl-5-cis-13-trans prostadienoic acid |
| 63 | dl-11α,16-dihydroxy-9-oxo-16-allenyl-20-methyl-5-cis-13-trans prostadienoic acid | dl-9β,11α,16-trihydroxy-16-allenyl-20-methyl-5-cis-13-trans prostadienoic acid |
| 64 | dl-11α,16-dihydroxy-9-oxo-16-allenyl-20-ethyl-5-cis-13-trans prostadienoic acid | dl-9β,11α,16-trihydroxy-16-allenyl-20-ethyl-5-cis-13-trans prostadienoic acid |
| 65 | dl-11α,16-dihydroxy-9-oxo-16-allenyl-20-nor-2-homo-5-cis-13-trans prostadienoic acid | dl-9β,11α,16-trihydroxy-16-allenyl-20-nor-2-homo-5-cis-13-trans prostadienoic acid |
| 66 | dl-11α,16-dihydroxy-9-oxo-16-allenyl-2-homo-5-cis-13-trans prostadienoic acid | dl-9β,11α,16-trihydroxy-16-allenyl-2-homo-5-cis-13-trans prostadienoic acid |
| 67 | dl-11β,16-dihydroxy-9-oxo-16-allenyl-20-methyl-2-homo-5-cis-13-trans prostadienoic acid | dl-9β,11α,16-trihydroxy-16-allenyl-20-methyl-2-homo-5-cis-13-trans prostadienoic acid |
| 68 | dl-11α,16-dihydroxy-9-oxo-16-allenyl-20-ethyl-2-homo-5-cis-13-trans prostadienoic acid | dl-9β,11α,16-trihydroxy-16-allenyl-20-ethyl-2-homo-5-cis-13-trans prostadienoic acid |
| 69 | nat-11α,16-dihydroxy-9-oxo-16-allenyl-20-nor-5-cis-13-trans prostadienoic acid | nat-9β,11α,16-trihydroxy-16-allenyl-20-nor-5-cis-13-trans prostadienoic acid |
| 70 | nat-11α,16-dihydroxy-9-oxo-16-allenyl-5-cis-13-trans prostadienoic acid | nat-9β,11α,16-trihydroxy-16-allenyl-5-cis-13-trans prostadienoic acid |
| 71 | nat-11α,16-dihydroxy-9-oxo-16-allenyl-20-methyl-5-cis-13-trans prostadienoic acid | nat-9β,11α,16-trihydroxy-16-allenyl-20-methyl-5-cis-13-trans prostadienoic acid |
| 72 | nat-11α,16-dihydroxy-9-oxo-16-allenyl-20-ethyl-5-cis-13-trans prostadienoic acid | nat-9β,11α,16-trihydroxy-16-allenyl-20-ethyl-5-cis-13-trans prostadienoic acid |

| EXAMPLE | STARTING PROSTAGLANDIN OF THE PGE SERIES | PRODUCT PROSTAGLANDIN OF THE 11-DEOXY PGF$_{2\beta}$ SERIES |
|---|---|---|
| 73 | dl-16-hydroxy-9-oxo-16-allenyl-20-nor-2-nor-5-cis-13-trans prostadienoic acid | dl-9β,16-dihydroxy-16-allenyl-20-nor-2-nor-5-cis-13-trans prostadienoic acid |
| 74 | dl-16-hydroxy-9-oxo-16-allenyl-2-nor-5-cis-13-trans prostadienoic acid | dl-9β,16-dihydroxy-16-allenyl-2-nor-5-cis-13-trans prostadienoic acid |
| 75 | dl-16-hydroxy-9-oxo-16-allenyl-20-methyl-2-nor-5-cis-13-trans prostadienoic acid | dl-9β,16-dihydroxy-16-allenyl-20-methyl-2-nor-5-cis-13-trans prostadienoic acid |
| 76 | dl-16-hydroxy-9-oxo-16-allenyl-20-ethyl-2-nor-5-cis-13-trans prostadienoic acid | dl-9β,16-dihydroxy-16-allenyl-20-ethyl-2-nor-5-cis-13-trans prostadienoic acid |
| 77 | dl-16-hydroxy-9-oxo-16-allenyl-20-nor-5-cis-13-trans prostadienoic acid | dl-9β,16-dihydroxy-16-allenyl-20-nor-5-cis-13-trans prostadienoic acid |
| 78 | dl-16-hydroxy-9-oxo-16-allenyl-5-cis-13-trans prostadienoic acid | dl-9β,16-dihydroxy-16-allenyl-5-cis-13-trans prostadienoic acid |
| 79 | dl-16-hydroxy-9-oxo-16-allenyl-20-methyl-5-cis-13-trans prostadienoic acid | dl-9β,16-dihydroxy-16-allenyl-20-methyl-5-cis-13-trans prostadienoic acid |
| 80 | dl-16-hydroxy-9-oxo-16-allenyl-20-ethyl-5-cis-13-trans prostadienoic acid | dl-9β,16-dihydroxy-16-allenyl-20-ethyl-5-cis-13-trans prostadienoic acid |
| 81 | dl-16-hydroxy-9-oxo-16-allenyl-20-nor-2-homo-5-cis-13-trans prostadienoic acid | dl-9β,16-dihydroxy-16-allenyl-20-nor-2-homo-5-cis-13-trans prostadienoic acid |
| 82 | dl-16-hydroxy-9-oxo-16-allenyl-2-homo-5-cis-13-trans prostadienoic acid | dl-9β,16-dihydroxy-16-allenyl-2-homo-5-cis-13-trans prostadienoic acid |
| 83 | dl-16-hydroxy-9-oxo-16-allenyl-20-methyl-2-homo-5-cis-13-trans prostadienoic acid | dl-9β,16-dihydroxy-16-allenyl-20-methyl-2-homo-5-cis-13-trans prostadienoic acid |
| 84 | dl-16-hydroxy-9-oxo-16-allenyl-20-ethyl-2-homo-5-cis-13-trans prostadienoic acid | dl-9β,16-dihydroxy-16-allenyl-20-ethyl-2-homo-5-cis-13-trans prostadienoic acid |

While specific embodiments of this invention have been described with particularity herein, it will be understood that the invention embraces all changes and modifications of the particular compounds chosen for purposes of illustration herein which do not depart from the spirit and scope of the invention.

I claim:

1. An optically active compound of the formula:

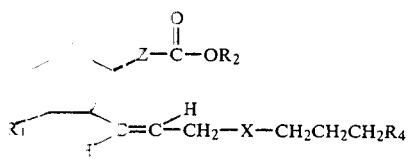

wherein X is

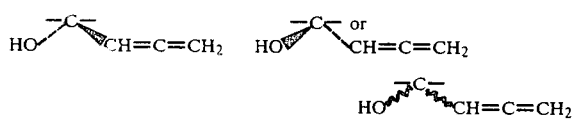

Y is:

$R_1$ is hydrogen or hydroxyl;
$R_2$ is hydrogen or $C_1$ to $C_6$ alkyl;
$R_4$ is hydrogen, $C_1$ to $C_3$ alkyl, or chlorine;
Z is

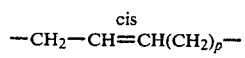

wherein p is 2 to 5, and the racemic mixture thereof; and when $R_1$ is hydrogen, the pharmaceutically acceptable salts thereof.

2. The racemic compounds according to claim 1, 11α,16α/β-dihydroxy-9-oxo-16-allenyl-5-cis,13-trans-prostadienoic acid, the individual 16α- and 16β-hydroxy racemates and the methyl esters thereof.

3. The optically active compounds according to claim 1, nat.-11α,16α/β-dihydroxy-9-oxo-16-allenyl-5-cis,13-trans-prostadienoic acid, the individual 16α- and 16β- hydroxy isomers, and the methyl esters thereof.

4. The optically active compound according to claim 3, nat.-11α,16α-dihydroxy-9-oxo-16-allenyl-5-cis,13-trans prostadienoic acid, methyl ester.

* * * * *